(12) United States Patent
Granja Guillán et al.

(10) Patent No.: US 7,618,999 B2
(45) Date of Patent: Nov. 17, 2009

(54) PROCESS OF OBTAINING TAXOSTEROIDS AND PRECURSORS THEREOF

(75) Inventors: Juan Granja Guillán, Santiago de Compostela (ES); Luis Castedo Expósito, Santiago de Compostela (ES); Rebeca García Fandiño, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 261 days.

(21) Appl. No.: 10/563,404

(22) PCT Filed: Jul. 2, 2004

(86) PCT No.: PCT/ES2004/000313

§ 371 (c)(1),
(2), (4) Date: Aug. 10, 2006

(87) PCT Pub. No.: WO2005/002496

PCT Pub. Date: Jan. 13, 2005

(65) Prior Publication Data

US 2007/0185108 A1    Aug. 9, 2007

(30) Foreign Application Priority Data

Jul. 4, 2003    (ES)    ................. 200301571

(51) Int. Cl.
*A61K 31/27*    (2006.01)
*A61K 31/216*    (2006.01)
*C07C 229/34*    (2006.01)
*C07C 271/12*    (2006.01)

(52) U.S. Cl. ................ 514/480; 514/511; 560/29; 560/39

(58) Field of Classification Search ............. 562/29, 562/39; 514/511, 480
See application file for complete search history.

(56) References Cited

OTHER PUBLICATIONS

Garcia-Fandiñet al. "Tandem RCM of Dienynes for the Construction of Taxol-Type Carbocyclic Systems" Organic Letters, 2004, vol. 6, No. 2, pp. 193-196.
Liu et al. "Design, Synthesis, and Bioactivities of Steroid-Linked Taxol Analogues as Potential Targeted Drugs for Prostate and Breast Cancer" J. Nat. Prod., 2004, vol. 67, pp. 152-159.
Verdier-Pinard et al. "A Steroid Derivative with Paclitaxel-Like Effects on Tubulin Polymerization" Molecular Pharmacology, 2000, vol. 57, pp. 568-575.
Villalva-Servin et al. "A Direct Carbometallation-Stereoselective Cycloaddition-Ring Closing Metathesis Route to the Tricyclis ABC Core of Taxoids" SYNLETT, Nov. 7, 2003, vol. 9, pp. 1263-1266.
Wang et al. "Synthesis of B-Ring Homologated Estradiol Analogues that Modulate Tubulin Polymerization and Microtubule Stability" J. Med. Chem., 2000, vol. 43, No. 12, pp. 2419-2429.
Codesido et al. "Toward and Analogue of he Transition State of $PreD_3$—$D_3$ Isomerization: Stereoselective Synthesis of Linearly Fused 6-8-6 Carbocyclic Systems" Org. Lett., 2002, vol. 4, No. 10, pp. 1651-1654.
Ojima et al. "Macrocycle Formation by Ring-Closing Metathesis. Application to the Syntheses of Novel Macrocyclic Taxoids" J. Am. Chem. Soc., 2000, vol. 122, No. 22, pp. 5343-5353.
Bourgeois et al. "Synthesis of BC Ring-Systems of Taxol by Ring-Closing Metathsis." *Synthesis*. No. 6. 2000. pp. 869-882.

(Continued)

*Primary Examiner*—Bernard Dentz
(74) *Attorney, Agent, or Firm*—Merchant & Gould P.C.

(57) ABSTRACT

The present invention relates to a process of obtaining taxosteroids and precursors thereof from the hydrindane bicyclic ring system. The compounds have a tetracyclic system which combines the structural characteristics of taxanes, such as the bicyclo[5.3.1]undecane system (cycles A and B), fused to a six-membered ring (C), and of steroids, such as the CD bicycle, the A ring and the side chain (Sc). The process of preparing the compounds and their application as compositions with pharmacological properties of interest are described.

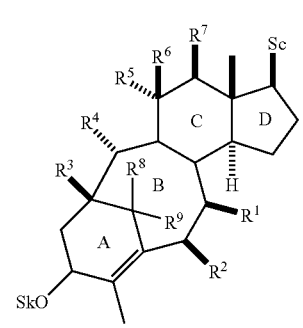

(1)

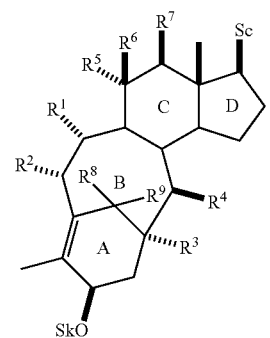

(2)

Taxosteroids

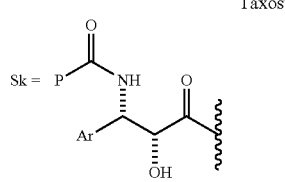

32 Claims, No Drawings

OTHER PUBLICATIONS

Codesido et al. "Access to [6.4.0]Carbocyclic Systems by Tandem Metathesis of Dienynes. A Step toward the Synthesis of a PreD-D Transition State Analogue." *Org. Lett.* vol. 3. No. 10. 2001. pp. 1483-1486.

Danishefsky et al. "Total Synthesis of Baccatin III and Taxol." *J. Am. Chem. Soc.* vol. 118. No. 12. 1996. pp. 2843-2859.

Deng et al. "A practical, highly enantioselective synthesis of the taxol side chain via asymmetric catalysis." *J. Org. Chem.* vol. 57. No. 15. 1992. pp. 4320-4323.

Denis et al. "An efficient, enantioselectice synthesis of the taxol side chain." *J. Org. Chem.* vol. 51. No. 1. 1986. pp. 46-50.

Denis et al. "An improved synthesis of the taxol side chain of RP 56976." *J. Org. Chem.* vol. 55. No. 6. 1990. pp. 1957-1959.

Denis et al. "Direct, highly, efficient synthesis from (S)-(+)-phenylglycine of the taxol and ataxotere side chains." *J. Org. Chem.* vol. 56. No. 24. 1991. pp. 6939-6942.

Furstner et al. "Coordinatively unsaturated ruthenium allenylidene complexes: highly effective, well defmed catlysts for the ring-closure metathesis of ci-w-dienes and dienynes." *Chem. Commun.* 1999. pp. 601-602.

Georg et al. "Taxane Anticancer Agents: Basic Science and Current Status." *ACS Symposium Series 583.* 1995. pp. ix-1.

Hamel et al. "The Coral-Dreived Natural Products Eleutherobin and Sarcodictyins A and B: Effects on the Assembly of Purified Tubulin with and without Microtubule-Associated Proteins and Binding at the Polymer Taxoid Site." *Biochemistry.* vol. 38. No. 17. 1999. pp. 5490-5498.

Hofle et al. "Epothilone A and B-Novel 16-Membered Macrolides with Cytotoxic Activity: Isolation, Crystal Structure, and Conformation in Solution."*Angew. Chem. Int. Ed. Engl.* vol. 35. No. 13/14. 1996. pp. 1567-1569.

Holton et al. "First total synthesis of taxol. 1. Functionalization of the B ring." *J. Am. Chem. Soc.* vol. 116. No. 4. 1994. pp. 1597-1600.

Jordan. "Mechanism of Action of Antitumor Drugs that Interact with Microtubules and Tubulin." *Curr. Med. Chem. - Anti-Cancer Agents.* vol. 2. 2002. pp. 1-17.

Kanazawa et al. "A short synthesis of the taxotere side chain through dilithiation of Boc-benzylamine."*J. Org. Chem.* vol. 58. No. 1. 1993. pp. 255-257.

Davis et al. "Assymmetric synthesis of sulfmimines: applications to the synthesis of nonracemic.beta-amino acides and.alpha.-hydroxyl.beta.-amino acids." *J. of Organic Chemistry.* vol. 57. No. 24. 1992. pp. 6387-6389.

Kim et al. "Catalytic Ring Closing Metathsis of Dienynes: Construction of Fused Bicyclic Rings." J. Am. Chem. Soc. vol. 116. No. 23. 1994. pp. 10801-10802.

Kim et al. "Catalytic Ring Closing Metathsis of Dienynes: Construction of Fused Bicyclic [n. m.0] Rings." *J. Org. Chem.* vol. 61. No. 3. 1996. pp. 1073-1081.

Kingston et al. "The Chemistry of Taxol and Related Taxoids." *Springer-Verlag Wein. New York.* 2002. pp. 53-225.

Kingston. "Taxol, a molecule for all seasons." *Chem. Commun.* 2001. pp. 867-880.

Long et al. "Eleutherobin, a Novel Cytotoxic Agent That Induces Tubulin Polymerizations, Is Similar to Paclitaxel (Taxole®)[1]" *Cancer Research.* vol. 58. 1998. pp. 1111-1115.

Mekhail et al. "Paclitaxel in cancer therapy." *Ashley Publications,* London. 2002. pp. 755-766.

Miller et al. "Chemistry and Chemical Biology of Taxane Anticancer Agents." *The Chem. Record.* vol. 1. 2001. pp. 195-211.

Nicolaou et al. "Total synthesis of taxol." *Nature.* vol. 367. 1994. pp. 630-634.

Nicolaou et al. "Total syntheses of complex nature products." *Agnew. Chem. Int. Ed. Engl.* vol. 34. No. 9. 1995. pp. 2069-2074.

Nicoletti et al. "IDN5109, a Taxane with Oral Bioavailability and Potent Antitumor Activity." *Cancer Research.* vol. 60. 2000. pp. 842-846.

Ojima et al. "Efficient and practical asymmetric synthesis of the taxol C-13 side chain, N-benzoyl-(2R,3S)-3-phenylisoserine, and its analogs via chiral 3-hydroxy-4-aryl-.beta.-lactams through chiral ester enolate-imine cyclocondensation." *J. Org. Chem.* vol. 56. No. 5. 1991. pp. 1681-1683.

Rowinsky et al. "Taxol: A Novel Investigational Antimicrotubule Agent." *J. of National. Cancer Int.* vol. 82. No. 15. 1990. pp. 1247-1259.

Scholl et al. "Synthesis and Activity of New Generation of Ruthenium-Based Olefin Metathesis Catalysts Coordinated with 1,3-Dimesity1-4-5-dihydroimidazol-2-ylidene Ligands." *Org. Letters.* vol. 1. No. 6. 1999. pp. 953-956.

Suffness. "Taxol Science and Applications." *CRC Press,* New York. 1995.

Wang et al. "Synthesis of B-Ring Homologated Estradiol Analogues that Modulated Tubulin Polymerization and Microtubule Stability." *J. Med. Chem.* vol. 43. No. 12. 2000. pp. 2419-2429.

Winkler et al. "Stereoselective Synthesis of the Taxane Ring System via the Tandem Diels - Alder Cycloaddion." *J. Org. Chem.* vol. 62. No. 9. 1997. pp. 2957-2962.

Wu et al. "Identification of a novel steroid derivative, NSC12983, as a paclitaxel-like tubulin assembly promoter by 3-D virtual screening." *Anti-Cancer Drug Design,* vol. 16. 2001. pp. 129-133.

Zuercher et al. "Ruthenium-Catalyzed Polycyclization Reactions." *J. Org. Chem.* vol. 63. No. 13. 1998. pp. 4291-4298.

Chabner et al. "Taxol." *Princ. Prac. Oncology,* vol. 5. No. 9. 1991. pp. 1-10.

PROCESS OF OBTAINING TAXOSTEROIDS AND PRECURSORS THEREOF

The present invention relates to the process of obtaining taxosteroids having a steroid and taxane hybrid structure; and of obtaining the intermediate precursors of said taxosteroids. The compounds are prepared from characteristic steroid hydrindane bicyclic ring systems.

Taxosteroids have the following formula:

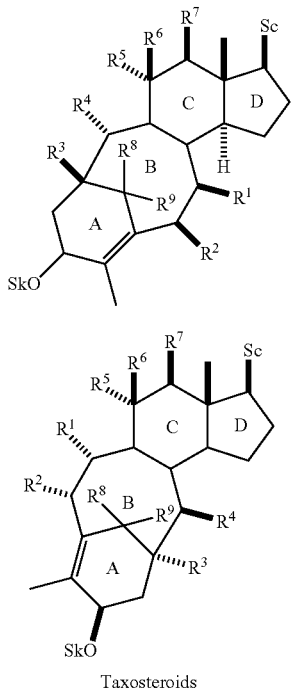

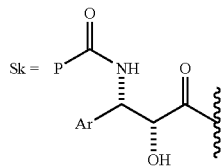

Taxosteroids in which $R^1$, $R^2$, $R^3$, $R^4$, $R^5$, $R^6$, $R^7$, $R^8$, $R^9$ and $R^{10}$ can be hydrogen or an acyloxy, alkyloxy or alkyl group with $C_1$-$C_{10}$ chains; Sc is the characteristic side chain of steroids; and Sk is an amino acid chain analogous to that of taxanes, in which Ar can be any aromatic compound and P an alkyloxy radical with $C_1$-$C_{10}$ chains.

Taxol (NSC 125973; paclitaxel; plaxicel; yewtaxan), Registry Number: [33069-62-4]; with molecular formula: $C_{47}H_{51}NO_{14}$, and absolute stereochemistry, (−) rotation:

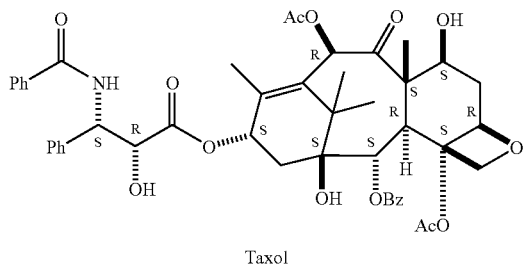

Taxol is a taxane-terpene derivative which was isolated in 1971 from the bark of *Taxus brevifolia* and which since 1992 has been used (approved by the FDA, US Food and Drug Administration) in the treatment of ovarian cancer metastasis and subsequently for the treatment of breast cancer (for a review on this matter see *Taxol: Science and Applications*; Suffness, M., Ed.; CRC: Boca Raton, Fla., 1995. Taxane Anticancer Agents: Basic Science and Current Status; Georg, G.II, Chen, T. T., Ojima, I., Vyaqs, D. M. Eds.; ACS Symposium Series 583; American Chemical Society: Washington, D.C., 1995). The mechanism of action is thought to imply the formation and hyperstabilization of microtubules and therefore the dissociation of the microtubules, an essential step for completing the cell division cycle, does not occur. It has also been published that taxol induces cytotoxin expression and that it affects quinase activity, blocking essential metastasis processes by means of a mechanism that has not yet been determined.

As a result, taxol has attracted the attention of scientists not only because of its unusual mechanism of action, but also because of its activity against all types of cancers that have been tested, and because it is a member of a family of natural substances, taxanes, having in common three basic rings (ABC), being different in the different substituents they have at the different positions of the carbocyclic skeleton:

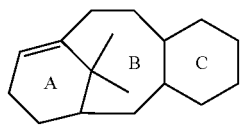

The most interesting analogues amongst them all are taxotere and IDN 5109.

Taxotere (docetaxel), Registry Number: [114977-28-5]; with molecular formula: $C_{43}H_{53}NO_{14}$ and absolute stereochemistry, has greater solubility and activity.

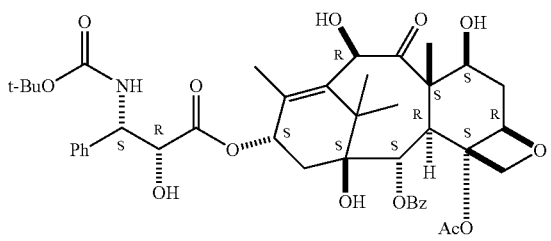

Taxotere

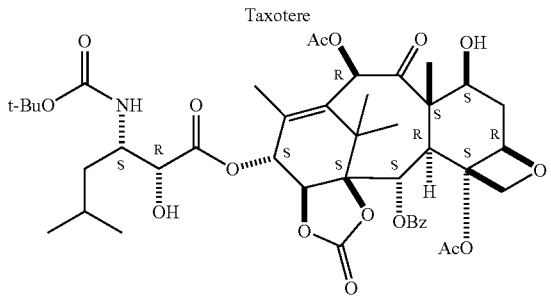

IDN 5109

IDN 5109 (ortataxel), Registry Number: [186348-23-2]; with molecular formula: $C_{44}H_{57}NO_{17}$ and absolute stereochemistry represented hereinbefore, is the first one with good oral bioavailability and potent antitumor activity (Nicoletti, M. I. et al. *Cancer Research,* 2000, 60, 842). Today these compounds are recognized as a new class of anticancer compounds.

An ideal anticancer agent must be selective for a certain tissue since it reduces the unwanted side effects on normal cells. Analogues with a higher specificity for tissues are therefore needed since this, along with its low solubility, is one of the drawbacks of taxol. To resolve this low solubility problem, taxol is usually administered dissolved in a mixture including cremophor, which mixture may cause immunological hypersensitivity.

In recent years over 200 taxanes have been synthesized and their anticancer activity has been studied both in vivo and in vivo, though the studies have not given rise to analogues that are more potent, more selective or more soluble, or with a better therapeutic index, no pattern allowing extracting a rule concerning their activity having been clearly found. Generally, the compounds having greater activity have as broad an action spectrum as taxol itself. Therefore it has not been possible to extract any pattern allowing predicting the positions that can be modified to improve their activity.

For reviews regarding taxol chemistry and pharmacology see the following reviews (Kingston, D. G. I.; Jagtap, P. G.; Yuan, H.; Samala, L. Progress in the Chemistry of Organic Products 2002, 84, 53-225. Mekhail, T. M.; Markman, M. Expert Opinion on Pharmacotherapy 2002, 3, 755-766. Miller, M. L.; Ojima, I. *Chemical Record,* 2001, 195-211. Kingston, D. G. I. *Chem. Commun.* 2001, 867. Nicolau, K. C.; Guy, R. K. *Angew. Chem. Int. Ed.* 1995, 34, 2079. Rowinsky, E. K.; Cazenave, L. A.; Donebower, R. C. J. Nati. Cancer Inst. 1990, 82,1247. Chabner, B. A. Princ. Prac. Oncol. 1991, 5, 1).

Different methods for both the total or partial preparation of taxol and derivatives thereof, as well as other taxanes, have recently been studied extensively.

The first total syntheses were described by Nicolau (*Nature* 1994, 367, 630) and Holton (*J. Am. Chem. Soc.* 1994, 116, 1597 and 1599) almost simultaneously. Nicolau's pathway is based on a convergent strategy in which the A and C rings are constructed separately and which are subsequently bonded at the bottom part of the skeleton by means of a Shapiro reaction. The B ring is subsequently completed by means of a McMurry reaction, the last steps being for D ring construction and introduction of the amino acid chain.

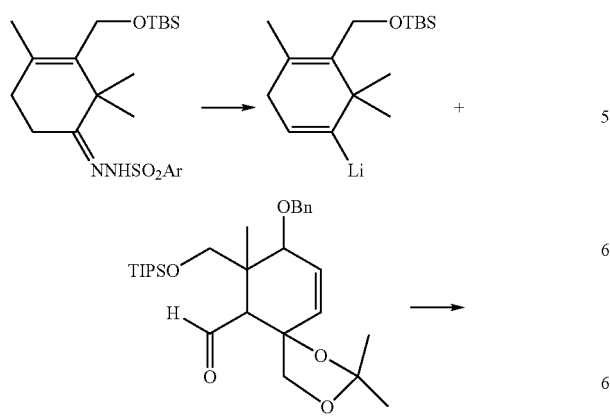

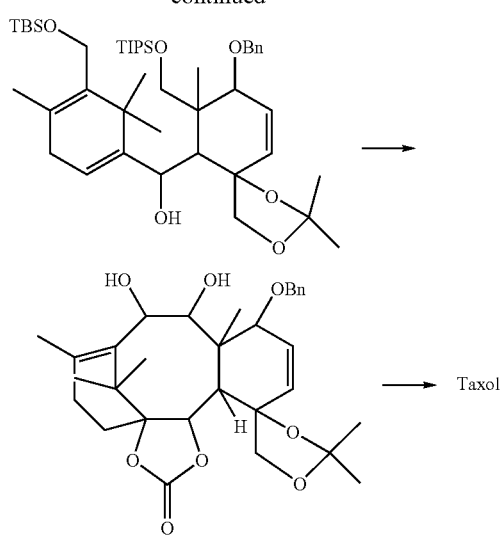

Holton's synthesis uses a linear strategy in which the ABCD rings are gradually constructed. The starting material used in this synthesis is borneol, which is transformed into an unsaturated tricyclic ketone which is subsequently converted into β-patchoulene oxide. From this an unsaturated carbocyclic derivative is obtained containing a tertiary alcohol. The subsequent epoxidation of this compound and the subsequent treatment of the resulting epoxide with a Lewis acid induces fragmentation to generate the A and B rings of taxol. The C ring is finally introduced on the previous bicyclic fragment, using a very tedious, Robinson-Stork type methodology.

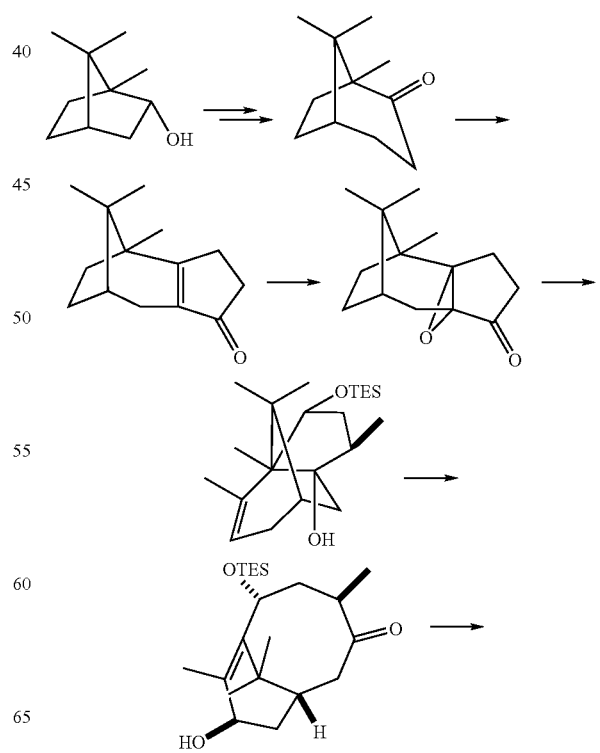

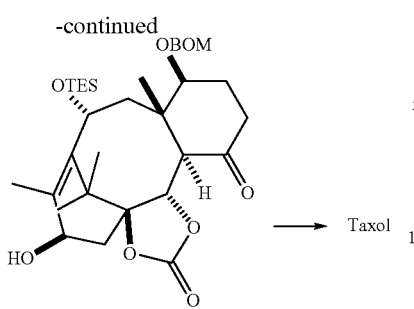

The third total synthesis was carried out by Prof. Danishefsky's group (*J Am. Chem. Soc.* (1996) 118, 2843) in which the Wieland-Miescher ketone was used as a starting material which, after a complex synthetic strategy, is transformed into an enol triflate containing the suitably functionalized C ring. The B ring of taxol is efficiently formed by means of Heck cyclization. Subsequent modifications allow introducing the amino acid side chain and dehydroxylation of the B ring.

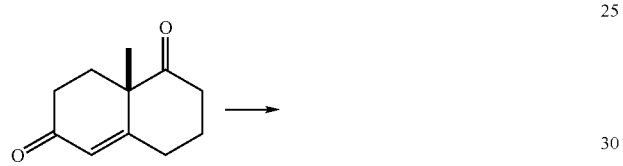

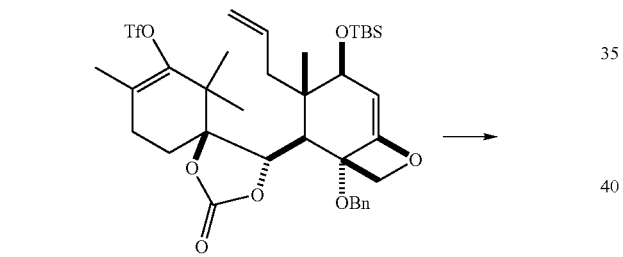

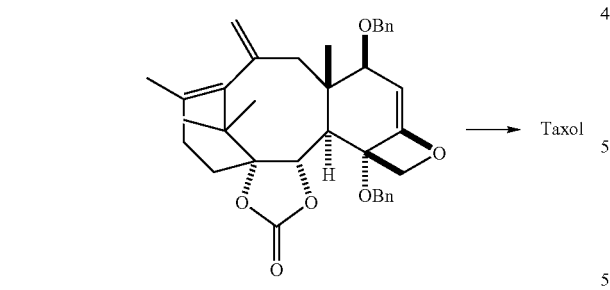

Other approaches for the synthesis of both taxol and of the polycyclic skeleton of taxanes subsequently appeared. Among the numerous strategies (see Kingston, D. G. I.; Jagtap, P. G.; Yuan, H.; Samala, L. Progress in the Chemistry of Organic Products 2002, 84, 53. Mekhail, T. M.; Markman, M. Expert Opinion on Pharmacotherapy 2002, 3, 755. Miller, M. L.; Ojima, I. *Chemical Record,* 2001, 195-211. Kingston, D. G. I. *Chem. Commun.* 2001, 867. Nicolau, K. C.; Guy, R. K. *Angew. Chem. Int. Ed.* 1995, 34, 2079. Rowinsky, E. K.; Cazenave, L. A.; Donebower, R. C. J. Natl. Cancer Inst. 1990, 82, 1247. Chabner, B. A. Princ. Prac. Oncol. 1991, 5, 1), it is necessary to mention the one based on a tandem Diels Alder cycloaddition (Jeffrey D. Winkler et al. *J. Org. Chem.* 1997, 62, 2957-2962), in which the B/C system of the taxane core is directly generated in two steps, and the one including metathesis reactions (Prunet, J.; Bourgeois, D.; Mahuteau, J.; Pancrazi, A.; Nolan, S. P.; *Synthesis* 2000, 6, 869).

In addition to these multiple syntheses, the most appropriate way to access both taxol and its analogues is through partial synthesis by means of modification of the most abundant natural derivatives, such as baccatin III and 10-deacetylbaccatin III (see examples: Journal of Organic chemistry: 1986, 51, 46; 1990, 55, 1957; 1991, 56, 1681; 1991, 56, 6939; 1992, 57, 4320; 1992, 57, 6387; and 1993, 58,255).

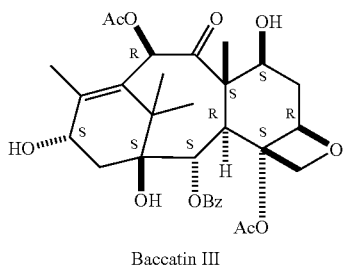

Baccatin III

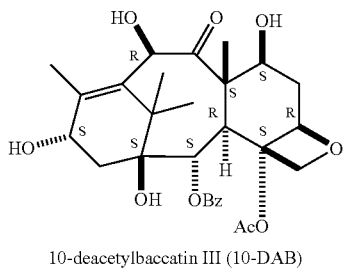

10-deacetylbaccatin III (10-DAB)

10-deacetylbaccatin III (10-DAB) is a natural taxane which is converted into taxol at a high yield by means of selective acetylation at C-10, silylation at C-7 and subsequent introduction of the side chain by reaction with the corresponding N-benzoyl-β-lactam. 10-DAB is mainly extracted from the needles of the European yew, *Taxus baccata*, and its isolation has several advantages with respect to that of taxol: on one hand, it is found in much higher concentrations than taxol in the bark of the trunk, and on the other hand, given that the needles regenerate through a prudent harvest process, high amounts of 10-DAB can be obtained without reducing the yew population. The yield of 10-DAB obtained from this source was about six to ten times greater than that of taxol from the bark of *Taxus brevifolia*. Furthermore, the isolation of 10-DAB, a tetraol, was significantly simpler and more economical than the isolation of taxol. The separation of taxol from a structural analogue, cephalomannine, was difficult, and whereas taxol must be isolated in a completely pure form for its direct incorporation in the medicinal product, 10-DAB must only be purified enough to be used as a starting material in the semi-synthesis.

There are other natural substances sharing the mechanism of action with taxanes, such as epothilones A and B (Hofle, G. et al. *Angew. Chem. Int. Ed. Eng.* 1996, 35, 1569), eleutherobin (Long, B.H. et al. *Cancer Research,* 1998, 58, 1111), sarcodictyins (Hamel, E. et al. *Biochemistry,* 1999, 38, 5490), etc. Steroid analogues have recently been discovered which are similar to paclitaxel in their ability to increase microtubule stability, such as the two 2-ethoxyestradiol analogues (Wang, Z. Q. et al. *J. Med. Chem.* 2000, 43, 2419), or NSC12983 (Wu, J. H. et al. *Anti-Cancer Drug Design* 2001, 16, 129), which confirms that this mechanism of action is not restricted to compounds with taxane structures and, therefore, confirms the need to continue investigating in this area (see review by Jordan, M. A. *Current Med. Chem.: Anti-Cancer Agents* 2002, 2,1).

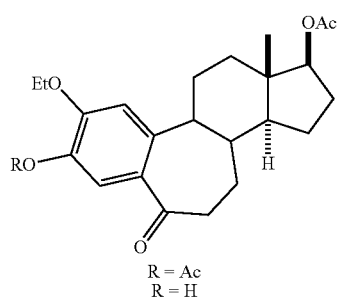

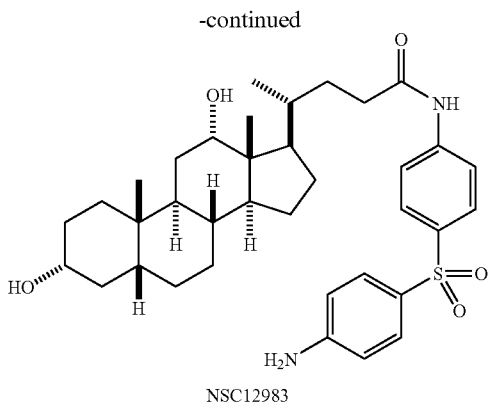

NSC12983

The present invention describes a class of compounds, taxosteroids, characterized by having a novel polycyclic system as a result of combining the carbocyclic skeletons of steroids and taxanes. As shown below, taxosteroids have the structural characteristics of taxanes, such as the bicyclo [5.3.1]-undecane system (cycles A and B) attached to a six-membered ring (C), and characteristics of steroids, such as the BD bicyclic ring system, the A ring and its side chain. Two possible types of analogues, formulas (1) and (2), considering the relative orientation between both components (steroid and taxane), are objectives of this invention, in which the $R^1$, $R^2$, $R^3$, $R^4$, $R^5$, $R^6$, $R^7$, $R^8$, $R^9$ and $R^{10}$ groups can be a hydrogen atom or an acyloxy, alkyloxy, aryloxy, alkylthio, arylthio or alkyl group with $C_1$-$C_{10}$ chains.

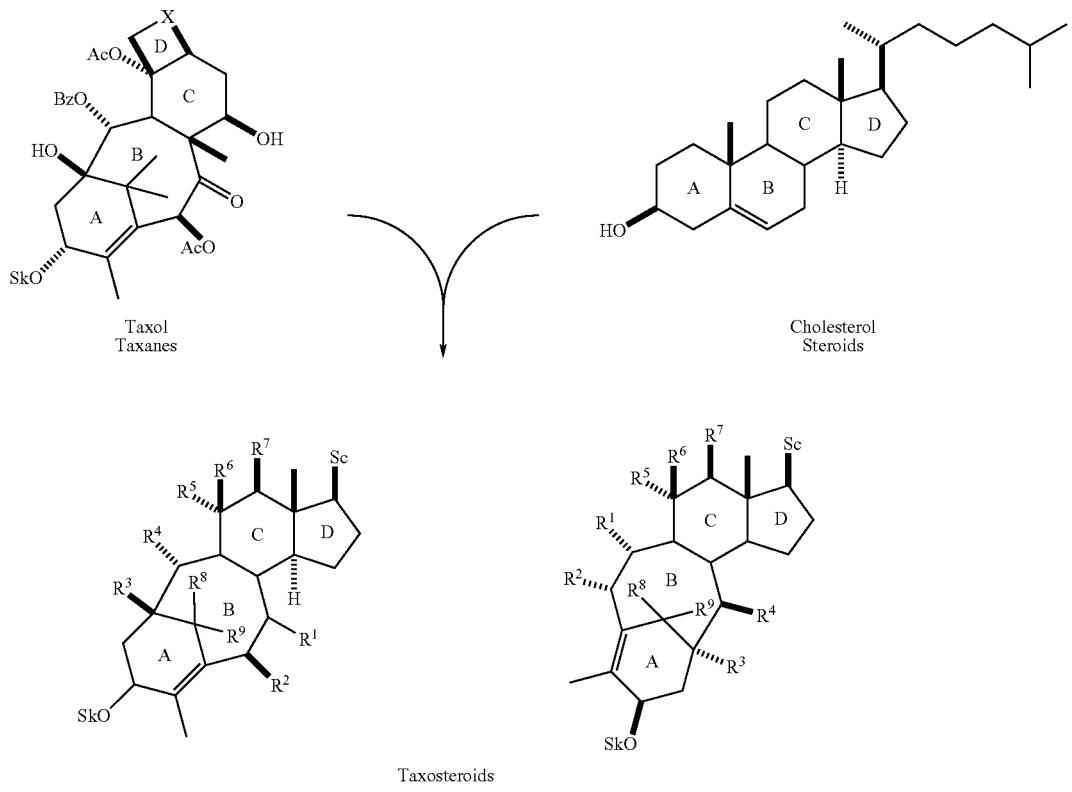

Taxosteroids

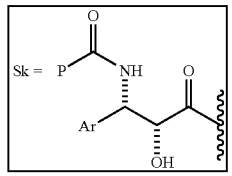

In all of them, the various substituents are radicals of the following type: linear or branched alkyl with 1-10 carbon atoms, alkenyl with 2 to 10 carbon atoms, alkynyl with 3 to 10 carbon atoms, cycloalkyl with 3 to 6 carbon atoms, cycloalkenyl with 4 to 6 carbon atoms or bicycloalkyl with 7 to 10 carbon atoms; these radicals possibly being substituted by one or several identical or different substituents chosen from halogen atoms and hydroxy, alkoxy radicals containing 1 to 4 carbon atoms, piperidinyl, morpholinyl, piperazinyl-1 (possibly substituted at −4 by an alkyl radical with 1 to 4 carbon atoms or by a phenylalkyl radical, the alkyl part of which contains 1 to 4 carbon atoms), cycloalkyl with 3 to 6 carbon atoms, cycloalkenyl with 4 to 6 carbon atoms, phenyl, cyano, nitro, carboxy or alkoxycarbonyl, the alkyl part of which contains 1 to 4 carbon atoms, or a phenyl radical, possibly substituted by one or several identical or different radicals, chosen from alkyl radicals with 1 to 4 carbon atoms or alkoxy radicals containing 1 to 4 carbon atoms, a saturated or unsaturated nitrogenous heterocyclic radical containing 5 or 6 members, possibly substituted by one or several alkyl radicals with 1 to 4 carbon atoms, understanding that the cycloalkyl, cycloalkenyl or bicycloalkyl radicals can possibly be substituted by one or several alky radicals containing 1 to 4 carbon atoms.

Sc is the characteristic side chain of steroids or a linear or branched alkyl radical with 1-12 carbon atoms, alkenyl with 2 to 12 carbon atoms, alkynyl with 3 to 12 carbon atoms, cycloalkyl with 3 to 6 carbon atoms, cycloalkenyl with 4 to 6 carbon atoms or bicycloalkyl with 7 to 10 carbon atoms; these radicals possibly being substituted by one or several identical or different substituents chosen from halogen atoms and hydroxy, alkoxy radicals containing 1 to 4 carbon atoms, piperidinyl, morpholinyl, piperazinyl-1 (possibly substituted at −4 by an alkyl radical with 1 to 4 carbon atoms or by a phenylalkyl radical, the alkyl part of which contains 1 to 4 carbon atoms), cycloalkyl with 3 to 6 carbon atoms, cycloalkenyl with 4 to 6 carbon atoms, phenyl, cyano, nitro, carboxy or alkoxycarbonyl, the alkyl part of which contains 1 to 4 carbon atoms, or a phenyl radical, possibly substituted by one or several identical or different radicals, chosen from alkyl radicals with 1 to 4 carbon atoms, or alkoxy radicals containing 1 to 4 carbon atoms, a saturated or unsaturated nitrogenous heterocyclic radical with 5 or 6 members, possibly substituted by one or several alkyl radicals with 1 to 4 carbon atoms, understanding that the cycloalkyl, cycloalkenyl or bicycloalkyl radicals can possibly be substituted by one or several alky radicals containing 1 to 4 carbon atoms.

Sk is an amino acid chain analogue to taxanes, in which P represents a phenyl group or an alkoxy radical with alkyl chains with 1 to 10 carbon atoms, alkenyl and alkynyl chains with 3 to 10 carbon atoms, cycloalkyl and cycloalkenyl chains with 4 to 7 atoms in the ring, a phenyl or a heterocyclic compound, and Ar is an aromatic compound.

Also object of the present invention are the analogue derivatives of the introduction of various substituents in the mentioned carbocyclic skeleton, as well as the pharmaceutical properties of the previously mentioned compounds, including their anticancer properties. Finally described is the process of obtaining said compounds.

The process of obtaining said compounds is based on a dienyne metathesis cyclization reaction, constructed on the steroid CD bicyclic ring system by means of simple transformations. The fundamental steps of these transformations consist of the alkylation of kinetic enolate of the ketone containing the characteristic and duly functionalized steroid CD bicyclic ring system, together with the corresponding side chain; the alylation of the carbonyl of the monoalkylated ketone obtained in the previous step, and finally, the resulting dienyne metathesis cyclization reaction (Kim, S. H.; Bowden, N.; Grubbs, R. H. *J. Am. Chem. Soc.* 1994, 116, 10801-10802; Kim, S. H.; Zuercher, W. J.; Bowden, N. B.; Grubbs, R. H. *J. Org. Chem.* 1996, 61, 1073-1081; Zuercher, W. J.; Scholl, M.; Grubbs, R. H. *J. Org. Chem.* 1998, 63, 4291-4298; Fürstner, A.; Liebl, M.; Hill, A. F.; Wilton-Ely, J. D. E. T. *Chem. Commun.* 1999, 601-602; Codesido, E. M.; Castedo, L.; Granja, J. R. *Org. Lett.* 2001, 3, 1483-1486).

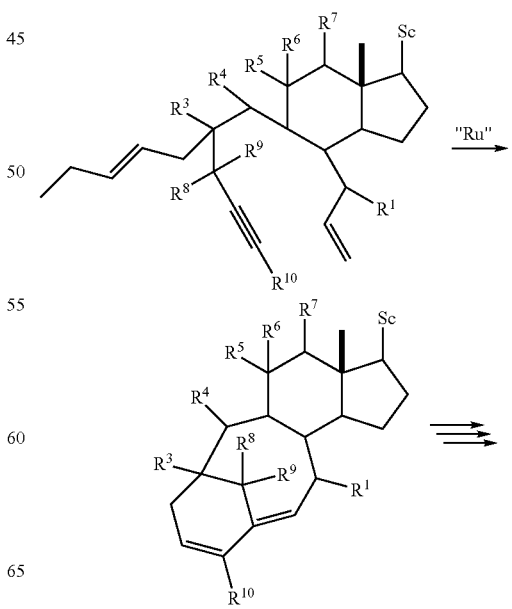

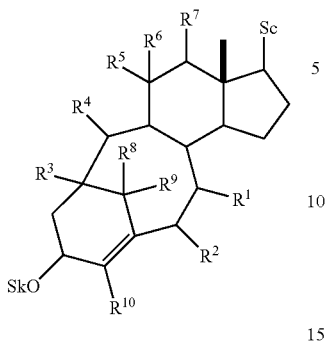

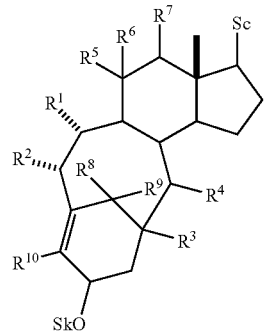

This novel cyclization for obtaining bicyclo[5.3.1]alkanes is based on a metathesis cyclization reaction catalyzed by metal carbene catalysts, among which Grubb's catalysts (Scholl, M.; Ding, S.; Lee, C. W.; Grubbs, R. H. *Org. Lett.* 1999, 1, 953-956) must be highlighted as the most important.

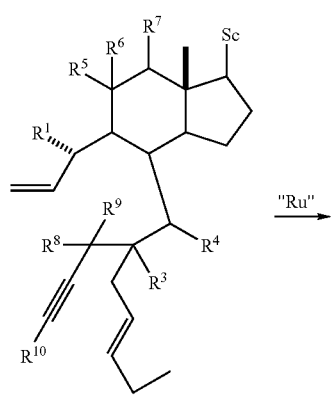

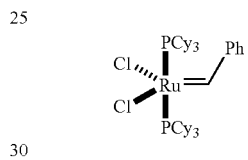

The reaction is based on an initial metathesis reaction between the catalyst and the least substituted olefin, generating the metal carbene intermediate II, which subsequently reacts with alkyne to form the central 8-membered cycle by means of an enyne cyclization reaction, generating a new metal carbene intermediate (III). The resulting intermediate III reacts with the other olefine by means of another metathesis cyclization to from the taxosteroid A ring. The structural characteristics of the P group allow controlling the region selectivity of the process, favoring process initiation by the least substituted olefine, which in turn favors the initial formation of the eight-membered ring. This group must likewise direct enyne cyclization against the dienyne cyclization that would give rise to compound V.

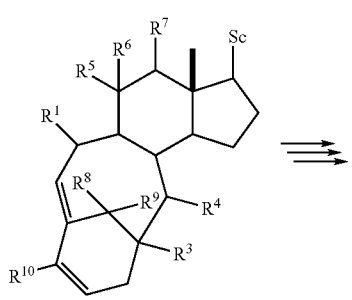

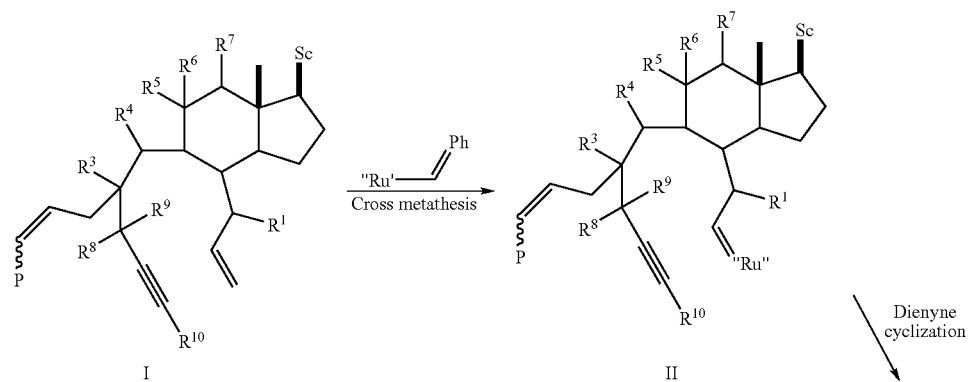

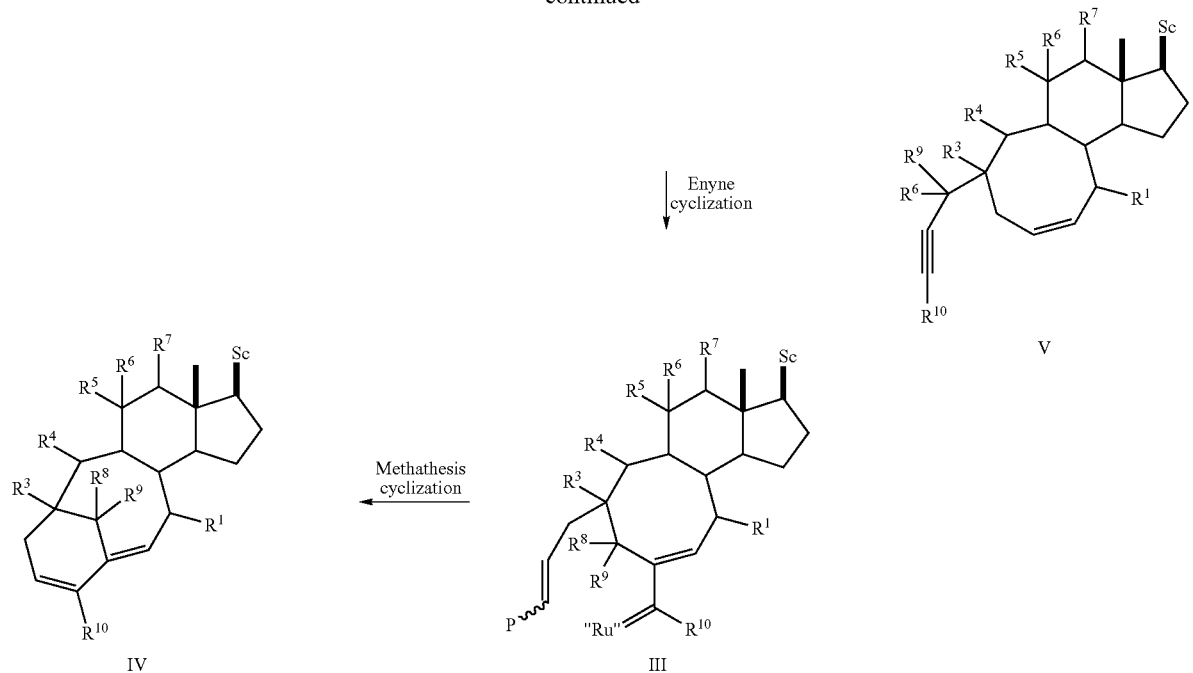

EXAMPLE 1

The taxosteroid (XIII) was prepared following the mentioned synthetic strategy, using ketone derived from the Inhoffen diol and the corresponding iodine derivative as starting substances. The alkylating agents can be prepared form the tricarboxy methane triethyl ester by means of alkylations with the suitable alkenyl and alkynyl derivatives. Thus, after the monopropargylation of the tricarboxy methane triethyl ester by treatment with sodium ethoxide and bromopropyne in THF, followed by treatment with sodium ethoxide in the presence of 1-bromo-4-methyl-2-pentene, the malonate diester VII is obtained by means of a process based on decarboxylation and subsequent alkylation of the resulting propargylmalonate enolate with the corresponding allyl bromide. The subsequent decarboxylation with sodium ethoxide in ethanol and reduction with lithium and aluminum hydride and transformation of the resulting alcohol into a good leaving group (iodine, mesylate, etc.) gives rise to the desired alkylating agents.

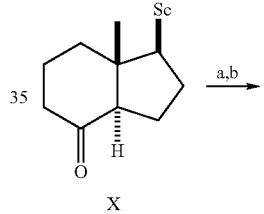

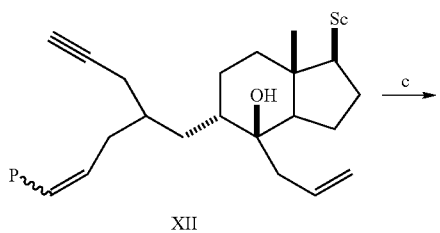

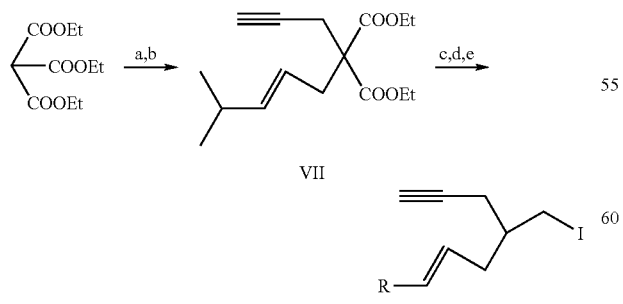

(a) NaOEt, BrCH$_2$C≡CH,THF, 85%; (b) NaOEt, BrCH$_2$CH═CH—R, 77–85%; (c) NaOEt, EtOH, 60–70%; (d) LiAlH$_4$, THF, 70–90%; (e) I$_2$, PPh$_3$, Imidazole, 86%;

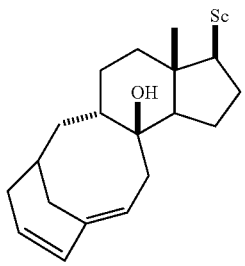

(a) i) KHDMS, DMF, -78° C., ii) 2-propargyl-1-iodo-4-heptene, 75%; (b) AlilMgBr, THF, 95%; (c) Grubb's catalyst, CH$_2$Cl$_2$, Δ, 87%.

Treatment of the ketone kinetic enolate of X, generated by treatment of said ketone with KHMDS, with the iodide IX and subsequent treatment of the resulting monoalkylated ketone with allylmagnesium bromide produces dienyne XII. The addition of the Grubb's catalyst to a solution of dienyne XII in dichloromethane and heating of the resulting mixture gives way to the taxosteroid Ill.

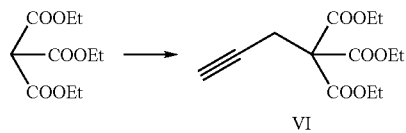

VI

A solution of sodium ethoxide (1.93 g, 28.42 mmol) in ethanol (24 mL) was added to a solution of the methane carboxylate triethyl ester (6.00 g, 25.84 mmol) in ether (20 mL) cooled in an ice/water bath. The resulting sodium salt that precipitates is collected, washed with ether and vacuum-dried to give 5.78 g of the desired salt which was dissolved in a toluene:DMF mixture (1:1, 50 mL) and treated with propargyl bromide (80% by weight of toluene, 5.1 mL, 45.5 mmol). The resulting mixture was heated at 80° C. for 1.5 hours, cooled at room temperature, filtered and the residue washed with toluene. The pooled filtrates were washed with water, dried over $Na_2SO_4$, filtered and concentrated. The resulting crude product was distilled (97° C. at 0.2 mmHg), yielding 6.03 g of but-3-yn-1,1,1-tricarboxylate triethyl ester (VI). $^1$H-NMR (CDCl$_3$, 300 MHz, δ): 4.25 (6H, c, J=7.1 Hz, 3 OC$\underline{H}_2$—Me), 2.98 (2H, d, J=2.6 Hz, H-2), 2.01 (1H, t J=2.6, H—C≡), 1.26 (9H, t, J=7.1 Hz, 3 OCH$_2$—C$\underline{H}_3$). $^{13}$C-NMR (CDCl$_3$, 75 MHz, δ): 165.6 (3 CO), 78.6 (C≡), 70.6 (C≡), 64.4 (C), 62.4 (3 CH$_2$), 23.1 (CH$_2$), 13.8 (3 CH$_3$). EM-IQ$^+$ (m/z, I): 271 (MH$^+$, 100), 197 (35), 125 (24); HRMS calculated for $C_{13}H_{19}O_6$ (MH$^+$): 271.118164, 271.118680 found.

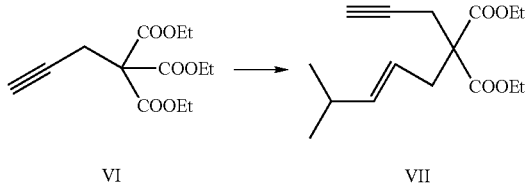

VI VII

A solution of but-3-yn-1,1,1-tricarboxylate triethyl ester (VI) (3.00 g, 11.10 mmol) in THF (3 mL) was added through a cannula to a suspension of sodium ethoxide (980 g, 14.4 mmol) in THF (35 mL). After 1.5 hours, (2E)-4-methyl-2-pentenyl methylsulfonate (3.9 g, 22.20 mmol) was added and the mixture was stirred at room temperature for 5 hours. After this time the reaction mixture was poured over a saturated NaCl solution and extracted with ether. The pooled organic phases were dried, filtered and concentrated and the residue was purified by means of flash chromatography (4% EtOAc/hexanes) to give 2.6 g of VII [88%, R$_f$=0.5 (15% EtOAc/hexanes)]. $^1$H-NMR (CDCl$_3$, 300 MHz, δ): 5.52 (1H, dd, J=6.9 Hz, J=15.2 Hz, $^1$Pr—C$\underline{H}$=CHR), 5.15 (1H, m, $^1$Pr—CH=CHR), 4.17 (4H, c, J=7.1 Hz, 2 CO$_2$C$\underline{H}_2$), 2.75 (2H, d, J=2.6 Hz, —C$\underline{H}_2$—C≡), 2.70 (2H, d, J=7.5 Hz, —C$\underline{H}_2$—C=), 2.21 (1H, m, Me$_2$C$\underline{H}$), 1.98 (1H, t, J=2.6 Hz, $\underline{H}$—C≡), 1.23 (6H, t, J=7.1 Hz, 2 CO$_2$CHC$\underline{H}_3$), 0.92 (6H, d, J=6.8 Hz, 2 CH$_3$). $^{13}$C-NMR (CDCl$_3$, 75 MHz, δ): 169.8 (2 CO), 143.2 (CH), 119.7 (CH), 79.1 (C≡), 71.2 (C≡), 61.5 (2 CH$_2$), 57.0 (C), 35.0 (CH$_2$), 31.1 (CH), 22.0 (2 CH$_3$), 21.7 (CH$_2$), 14.1 (2 CH$_{3h}$). EM-IQ$^+$ (m/z, I): 281 (MH$^+$, 58), 207 (25), 133 (17); HRMS calculated for $C_{16}H_{25}O_4$ (MH$^+$): 281.175285, 281.175641 found.

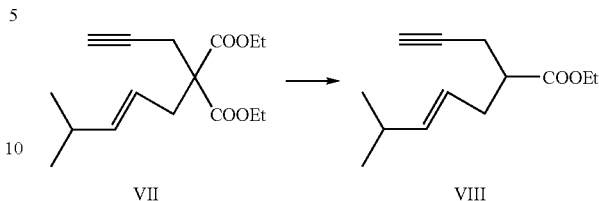

VII VIII

A solution of compound VII (3.2 g, 12.01 mmol) was added to a solution of EtONa (1.23 g, 18.07 mmol) in ethanol (50 mL). The reaction mixture was heated under reflux for 2 days and once this time elapsed it was poured over NaCl (40 mL). The mixture was acidified with 10% HCl (20 mL) and extracted with ether. The pooled organic phase was dried with Na$_2$SO$_4$, filtered, concentrated and the residue purified by means of silica gel flash chromatography (1% EtOAc/hexanes) to give 1.3 g of the ester VIII [50%, R$_f$=0.5 (15% EtOAc/hexanes), yellow oil]. $^1$H-NMR (CDCl$_3$, 250 MHz, δ): 5.47 (1H, dd, J=6.3 Hz, J=15.5 Hz, H-5), 5.26 (1H, m, H-4), 4.15 (2H, c, J=7.1 Hz, —CO$_2$—C$\underline{H}_2$—), 2.56 (1H, m, H-6), 2.33 (5H, m, H-3, H-2, C$\underline{H}_2$—C≡), 1.98 (1H, t, J=2.6 Hz, H-C≡), 1.26 (3H, t, J=7.1 Hz, —CO$_2$—CH$_2$—C$\underline{H}_3$), 0.94 (6H, d, J=6.8 Hz, 2×$^1$Pr Me). $^{13}$C-NMR (CDCl$_3$, 63 MHz, δ): 173.5 (CO), 140.7 (CH), 122.3 (CH), 81.2 (C≡), 69.6 (C≡), 60.1 (CH$_2$), 44.3 (CH), 33.8 (CH$_2$), 30.8 (CH), 22.2 (2 CH$_3$), 19.9 (CH$_2$), 14.0 (CH$_3$); EM-IQ$^+$(m/z, I): 209 (MH$^+$, 29), 136 (MH$^+$—CO$_2$Et, 2); HRMS calculated for $C_{13}H_{21}O_2$ (MH$^+$): 209.154155, 209.154326 found.

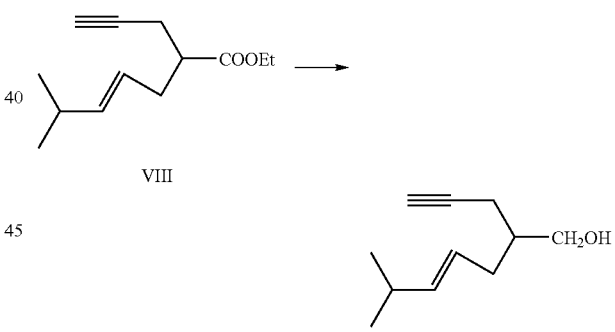

VIII

A solution of ester VIII (290 mg, 1.49 mmol) in ether (10 mL), cooled at 0C, was treated with LiAlH$_4$ (113 mg, 2.99 mmol). The resulting mixture was stirred for 1 hour, 5% H$_2$SO$_4$ (5 mL) was then added and extracted with ether. The ether phases were dried, filtered, concentrated and the resulting crude product purified by means of silica gel flash chromatography (10% EtOAc/hexanes), giving 210 g of 6-methyl-2-prop-2-inyl-4-hepten-1-ol [89%, R$_f$=0.3 (15% EtOAc/hexanes)]. $^1$H-NMR (CDCl$_3$, 300 MHz, δ): 5.45 (1H, dd, J=6.4 Hz, J=15.3 Hz, H-5), 5.30 (1H, dt, J=7.1 Hz, J=15.2 Hz, H-4), 3.62 (2H, m, H-1), 2.24 (1H, m, H-6), 1.96 (1H, t, J=2.6 Hz, H-C=), 1.76 (1H, m, H-2), 0.95 (6H, d, J=6.7 Hz, 2 CH$_3$). $^{13}$C-NMR (CDCl$_3$, 75 MHz, 6): 140.3 (CH), 124.0 (CH), 82.6 (C≡), 69.7 (C≡), 64.8 (CH$_2$), 40.0 (CH), 33.6 (CH$_2$), 31.0 (CH), 22.6 (2 CH$_3$), 19.8 (CH$_2$). EM-IQ$^+$(m/e, I): 167 (MH$^+$, 31), 149 (MH$^+$—H$_2$O, 51); HRMS calculated for $C_{11}H_{19}O$ (MH$^+$): 167.143590, 167.144312 found.

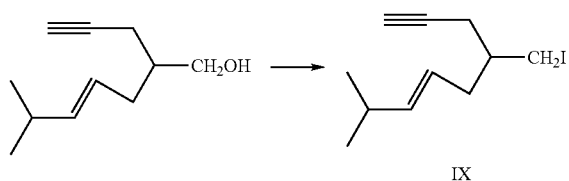

Triphenylphosphine (2.85 g, 10.87 mmol), imidazole (1.85 g, 27.17 mmol) and iodine (2.53 g, 9.96 mmol) were successively added to a solution of alcohol (1.5 g, 9.0 mmol) in THF (45 mL), cooled at 0° C. The resulting mixture was stirred at this temperature for 30 minutes and at room temperature for another 30 minutes, and it was subsequently poured over water and extracted with ether. The pooled organic phase was dried with $Na_2SO_4$, filtered and concentrated under reduced pressure, and the resulting residue was purified by means of silica gel flash chromatography to give iodide IX with an 85% yield, $R_f$=0.9 (10% EtOAc/hexanes), colorless oil. $^1$H-NMR (CDCl$_3$, 250 MHz, δ): 5.55 (1H, dd, J=6.6 Hz, J=15.3 Hz, H-7), 5.26 (1H, m, H-6), 3.36 (2H, m, —CH$_2$—I), 2.00 (1H, t, J=2.6 Hz, H—C≡), 1.50 (1H, m, H-4), 0.89 (6H, d, J=6.8 Hz, 2×$^i$Pr Me). $^{13}$C-NMR (CDCl$_3$, 63 MHz, δ): 141.1 (CH), 122.8 (CH), 81.4 (C≡), 70.1 (C≡), 38.9 (CH), 36.5 (CH$_2$), 31.0 (CH), 23.3 (CH$_2$), 22.5 (CH$_3$×2), 13.1 (CH$_2$). EM-IQ$^+$ (m/e, I): 277 (MH$^+$, 2), 150 (MH$^+$—I, 2).

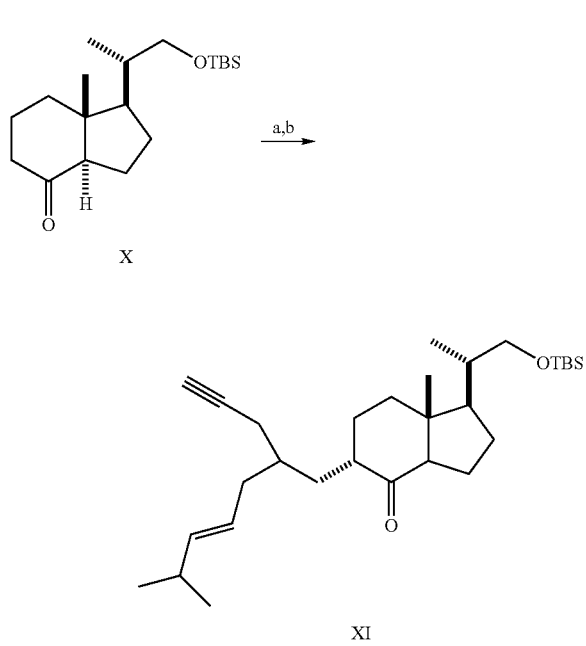

A solution of ketone X (0.5 g, 1.54 mmol) in DMF (3 mL) was slowly added to a solution of KHMDS (0.5 M in toluene, 9.3 mL, 4.6 mmol) in DMF (4 mL) cooled at −78° C. The resulting mixture was stirred at this temperature for 30 minutes and a solution of iodide IX (1.3 mg, 4.6 mmol) in DMF (2 mL) was then added. After two hours a saturated NH$_4$Cl solution (4 mL) was added and the aqueous phase was extracted with ether. The pooled ether extracts were washed with a saturated NaCl solution, were dried over Na$_2$SO$_4$, and concentrated under reduced pressure to give a residue that was purified by means of silica gel flash chromatography (2% EtOAc/hexanes), giving the desired product Xl with a 78% yield. $^1$H-NMR (CDCl$_3$, 250 MHz, δ): 5.41 (1 H, dd, J=6.4 Hz, J=15.3 Hz, H-5'), 5.22 (1H, m, H-4'), 3.51 (1H, m, —CH$_a$—OTBS), 3.31 (1H, m, —CH$_b$—OTBS), 2.57 (1H, m, H-6'), 0.87 (9H, s, $^t$Bu), 0.62 (3H, s, Me-18), 0.01 (6H, s, Me$_2$Si). $^{13}$C-NMR (CDCl$_3$, 63 MHz, δ): 214.6 (CO), 140.4 (CH), 124.1 (CH), 82.2 (C≡), 69.7 (C≡), 67.5 (CH$_2$), 57.6 (CH), 53.2 (CH), 50.3 (C), 47.2 (CH), 38.5 (CH), 36.4 (CH$_2$), 35.7 (CH$_2$), 35.4 (CH$_2$), 34.9 (CH), 31.1 (CH), 29.3 (CH$_2$), 27.0 (CH$_2$), 25.9 (2 CH$_3$), 22.6 (3 CH$_3$), 21.3 (CH$_2$), 19.0 (CH$_2$), 18.3 (C), 17.0 (CH$_3$), 12.8 (CH$_3$), −5.4 (2 CH$_3$). EM-IQ$^+$ (m/e, I): 473 (MH$^+$, 100), 342 (MH$^+$—OTBS, 6), 341 (28), 323 (12). HRMS calculated for C$_{30}$H$_{53}$O$_2$Si (MH+): 473.381485, 473.383792 found.

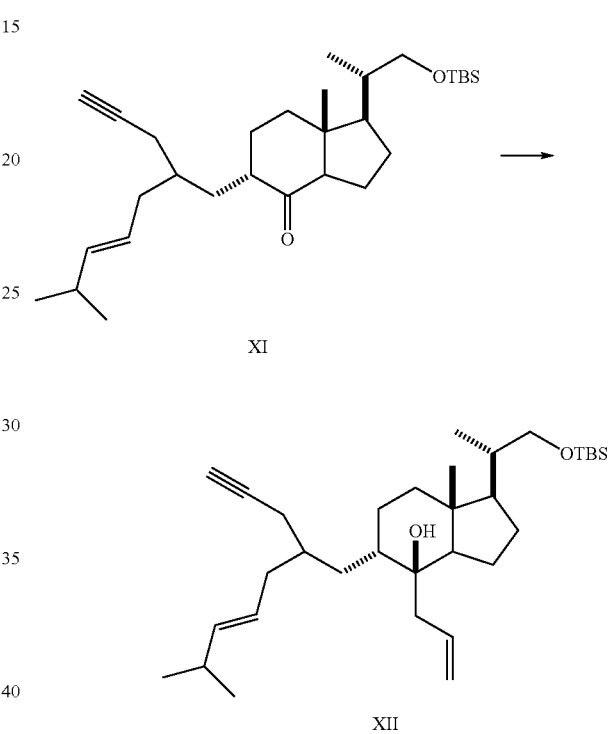

A solution of allylmagnesium bromide (1 M in THF, 4.7 mL, 4.7 mmol) was added to a solution of ketone Xl (520 mg, 1.1 mmol) in THF (10 mL) at −78° C. After two hours a saturated NH$_4$Cl solution (15 mL) was added and the aqueous phase was extracted with ether. The pooled ether extracts were washed with a saturated NaCl solution, were dried over Na$_2$SO$_4$, and concentrated under reduced pressure to give a residue that was purified by means of silica gel flash chromatography (3% EtOAc/hexanes), giving the desired product XII with a 90% yield. $R_f$=0.37 (10% EtOAc/hexanes). $^1$H-NMR (CDCl$_3$, 500 MHz, δ): 5.98 (1H, m, H-6) 5.46, 5.29 (2H, m, H-4', H-5'), 5.15 (2H, m, H-6a), 3.56 (1H, dd, J=3.2 Hz, J=9.6 Hz, —CH$_a$—OTBS), 3.25 (1H, dd, J=7.5 Hz, J=9.5 Hz, —CH$_b$—OTBS), 0.88 (9H, s, $^t$Bu), 0.02 (6H, s, Me$_2$Si). $^{13}$C-NMR (CDCl$_3$, 125 MHz, δ): 133.6 (CH), 133.3 (CH), 126.8 (CH), 119.7 (CH$_2$), 82.5 (C≡), 75.8 (C≡), 69.8 (CH$_2$), 67.7 (C), 53.7 (CH), 51.2 (CH), 43.5 (CH$_2$), 43.3 (C), 39.8 (CH), 38.5 (CH), 34.8 (CH), 34.6 (CH$_2$), 32.2 (CH$_2$), 30.8 (CH$_2$), 26.7 (CH$_2$), 26.0 (CH$_3$×3), 21.1 (CH$_2$), 20.7 (CH$_2$), 20.4 (CH$_2$), 20.3 (CH$_2$), 18.4 (C), 16.7 (CH$_3$), 14.3 (CH$_3$), 13.5 (CH$_3$), −5.3 (CH$_3$), −5.4 (CH$_3$). EM-IQ$^+$ (m/e, I): 501 (MH$^+$, 0.05), 352 (MH$^{30}$—OTBS—H$_2$O, 2). HRMS calculated for C$_{32}$H$_{57}$O$_2$Si (MH$^+$): 501.412785, 501.413082 found.

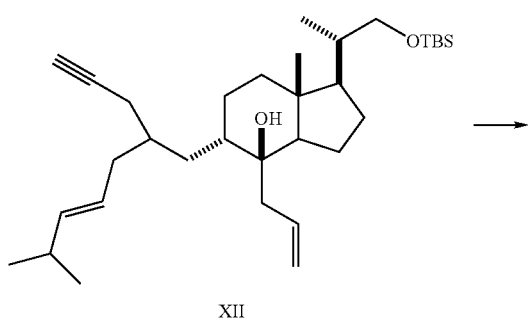

XII

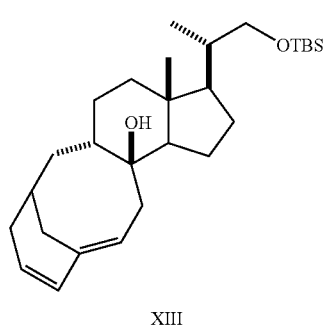

XIII

A solution of dienyne XII (200 mg, 0.35 mmol) in dichloromethane (80 mL) was treated with the Grubb's catalyst (34 mg, 0.04 mmol). The resulting mixture was heated at 50° C. for 24 hours and after cooling at room temperature was concentrated under reduced pressure. The resulting crude product was purified by means of aluminum chromatography (3% EtOAc/hexanes), to give the desired bicyclic compound XIII with a 55% yield. $R_f$=0.27 (10% EtOAc/hexanes). $^1$H-NMR (CDCl$_3$, 500 MHz, δ): 6.18 (1H, d, J=10.1 Hz, H-4) 5.43 (1H, m, H-3), 5.34 (1H, t, J=8.1 Hz, H-6), 3.61 (1H, dd, J=3.5 Hz, J=9.6 Hz, —CH$_a$—OTBS), 3.20 (1H, m, —CH$_b$—OTBS), 2.87 (1H, dd, J=3.9 Hz, J=11.4 Hz, H-10), 2.01 (1H, d, J=11.4 Hz, H-10), 0.91 (9H, s, $^t$Bu), 0.05 (3H, s, Me$_2$Si). $^{13}$C-NMR (CDCl$_3$, 125 MHz, δ): 139.7 (C), 130.5 (CH), 125.8 (CH), 119.1 (CH), 81.2 (C), 67.8 (CH$_2$), 53.8 (CH), 48.5 (CH), 45.2 (CH), 43.7 (C), 40.5 (CH$_2$), 38.6 (CH), 35.6 (CH$_2$), 35.1 (CH$_2$), 34.9 (CH), 33.3 (CH$_2$), 30.4 (CH$_2$), 29.9 (CH$_2$), 26.5 (CH$_2$), 26.0 (3 CH$_3$), 20.6 (CH$_2$), 18.4 (C), 16.4 (CH$_3$), 14.0 (CH$_3$), −5.3 (2 CH$_3$). EM-IQ$^+$ (m/e, I): 445 (MH$^+$, 4), 313 (4), 295 (83). HRMS calculated for C$_{28}$H$_{49}$O$_2$Si (MH+): 445.350185, 445.351417 found.

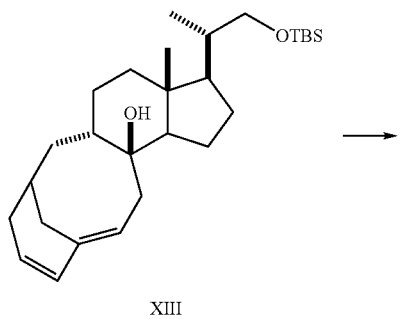

XIII

-continued

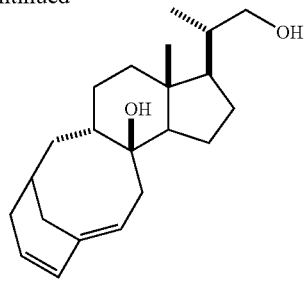

XIV

A solution of FTBA in THF (1 M, 2.2 mL, 2.2 mmol) was added to a solution of XIII (80 mg, 0.16 mmol) in THF (2 mL) and the resulting mixture was stirred under reflux for 1 hour. Once cooled at room temperature it was treated with NH$_4$Cl (10 mL) and extracted with ethyl ether (2×10 mL). The pooled organic phases were dried, filtered and concentrated under reduced pressure, and the resulting residue was purified by means of silica gel flash chromatography (25% EtOAc/hexanes), giving 48 mg of XIV with a 95% yield. $R_f$=0.36 (30% EtOAc/hexanes). $^1$H-NMR (CDCl$_3$, 300 MHz, δ): 5.84, 5.56 (2H, m, H-6, H-5), 3.59 (1H, m, —CH$_a$—OH), 3.33 (1H, m, —CH$_b$—OH), 1.94 (1H, t, J=2.6 Hz, H-C≡), 1.02 (3H, d, J=6.6 Hz, Me-21), 0.94 (3H, s, Me-18). $^{13}$C-NMR (CDCl$_3$, 75 MHz, δ): 131.6 (CH), 127.9 (CH), 83.6 (C≡), 78.4 (C), 70.0 (C≡), 68.2 (CH$_2$), 53.8 (CH), 52.2 (CH), 43.6 (C), 42.1 (CH), 41.0 (CH$_2$), 40.6 (CH), 38.6 (CH), 37.2 (CH$_2$), 35.5 (CH$_2$), 33.8 (CH$_2$), 30.1 (CH$_2$), 28.4 (CH$_2$), 27.1 (CH$_2$), 20.4 (CH$_2$), 16.9 (CH$_3$), 13.5 (CH$_3$). EM-IQ$^+$ (m/e, I): 331 (MH$^+$, 9), 313 (MH$^+$, H$_2$O, 75), 295 (MH$^+$—2H$_2$O, 100). HRMS calculated for C$_{22}$H$_{35}$O$_2$ (MH$^+$): 331.263706, 331.264789 found.

EXAMPLE 2

The taxosteroid (XVIII) was prepared in the following manner:

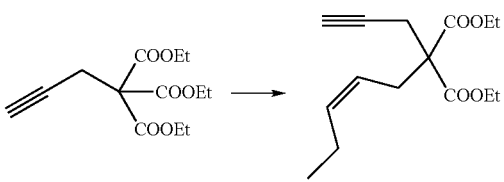

VI            VIIb

A solution of but-3-yn-1,1,1-tricarboxylate triethyl ester (VI) (5.0 g, 18.4 mmol) in THF (5 mL) was added through a cannula to a suspension of sodium ethoxide (1.48 g, 23.8 mmol) in THF (50 mL). After 1.5 hours, (2Z)-2-pentenyl methylsulfonate (5.9 g, 36.80 mmol) was added and the mixture was stirred at room temperature for 5 hours. After this time the reaction mixture was poured over a saturated NaCl solution and extracted with ether. The pooled organic phases were dried, filtered and concentrated and the residue was purified by means of flash chromatography (4% EtOAc/hexanes) to give 1.7 mg of VIIb [35%, $R_f$=0.6 (10% EtOAc/ hexanes)]. $^1$H-NMR (CDCl$_3$, 250 MHz, δ): 5.48 (1H, m, H-C=), 4.97 (1H, m, H-C=), 4.11 (4H, m, 2 CO$_2$CH$_2$), 2.70 (4H, m, —CH$_2$—C≡, CH$_2$—C=), 2.07 (2H, m, CH$_3$—CH$_2$—C=), 1.94 (1H, t, J=2.7 Hz, H-C≡), 1.18 (6H, t, J=7.15 Hz, 2 CO$_2$CH$_2$CH$_3$), 0.88 (3H, t, J=7.5 Hz, CH$_3$—CH$_2$—C=). $^{13}$C-NMR (CDCl$_3$, 63 MHz, δ): 169.7 (2 CO), 136.4 (CH), 121.6 (CH), 78.9 (C≡), 71.1 (C≡), 61.4 (CH$_2$), 61.1 (CH$_2$), 56.5 (C), 29.5 (CH$_2$), 22.2 (CH$_2$), 20.5 (CH$_2$), 14.0 (CH$_3$), 13.9 (CH$_3$), 13.6 (CH$_3$). EM-IQ$^+$ (m/z, I): 267 (MH$^+$, 100), 194 (MH$^+$—CO$_2$Et, 5), 121 (MH$^+$—(CO$_2$Et)$_2$, 5); HRMS calculated for C$_{15}$H$_{23}$O$_4$ (MH$^+$): 267.159634, 267.160073 found.

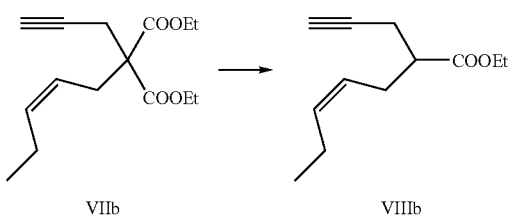

VIIb          VIIIb

A solution of compound VIIb (1.5 g, 5.61 mmol) was added to a solution of EtONa (570 mg, 8.4 mmol) in ethanol (20 mL). The reaction mixture was heated under reflux for 2 days and once this time elapsed was poured over NaCl (20 mL). The mixture was acidified with 10% HCl (20 mL) and extracted with ether. The pooled organic phase was dried with Na$_2$SO$_4$, filtered, concentrated and the residue purified by means of silica gel flash chromatography (1% EtOAc/hexanes), giving 600 mg of ester VIIIb [55%, R$_f$=0.6 (10% EtOAc/hexanes), yellow oil]. $^1$H-NMR (CDCl$_3$, 250 MHz, δ): 5.44 (1H, m, H-C=), 5.19 (1H, m, H-C=), 4.11 (2H, c, J=7.1 Hz, —CO$_2$—CH2), 2.51 (1H, m, H-2), 2.35 (4H, m, H-3, CH$_2$—C=), 2.01 (3H, m, H-6, H-C=), 1.21 (3H, t, J=7.1 Hz, —CO$_2$—CH$_2$—CH$_3$), 0.90 (3H, T, J=7.5 Hz, H-7). $^{13}$C-NMR (CDCl$_3$, 63 MHz, δ): 173.8 (CO), 134.6 (CH), 124.3 (CH), 81.4 (C≡), 69.8 (C≡), 60.5 (CH$_2$), 44.4 (CH), 28.5 (CH$_2$), 20.5 (CH$_2$), 20.3 (CH$_2$), 14.2 (CH$_3$), 14.1 (CH$_3$). EM-IQ$^+$ (m/z, I): 195 (MH$^+$, 53), 167 (27), 149 (17), 121 (100). HRMS calculated for C$_{12}$H$_{19}$O$_2$ (MH$^+$): 195.138505, 195.138842 found.

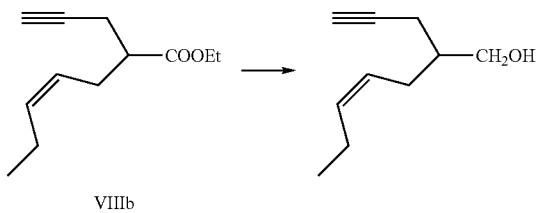

VIIIb

A solution of ester VIIIb (500 mg, 2.56 mmol) in ether (20 mL), cooled at 0° C., was treated with LiAlH$_4$ (150 mg, 4.0 mmol). The resultung mixture was stirred for 1 hour, 5% H$_2$SO$_4$ (10 mL) was then added and was extracted with ether. The pooled ether phases were dried, filtered and concentrated and the resulting crude product purified by means of silica gel flash chromatography (10% EtOAc/hexanes), giving 352 mg of 2-prop-2-inyl-4-hepten-1-ol [90%, R$_f$=0.15 (15% EtOAc/hexanes)]. $^1$H-NMR (CDCl$_3$, 250 MHz, δ): 5.45 (2H, m, H-4, H-5), 3.61 (2H, m, H-1), 2.25 (1H, m, H-6), 2.13 (4H, m, CH$_2$—C≡, H-3), 1.96 (1H, t, J=2.7 Hz, H-C≡), 1.75 (1H, m, H-2), 0.93 (3H, t, J=7.5 Hz, H-7). $^{13}$C-NMR (CDCl$_3$, 63 MHz, δ): 133.9 (CH), 126.0 (CH), 82.5 (C≡), 69.7 (C≡), 64.7 (CH$_2$), 40.2 (CH), 28.0 (CH$_2$), 20.6 (CH$_2$), 19.8 (CH$_2$), 14.2 (CH$_3$). EM-IQ$^+$ (m/e, I): 153 (MH$^+$, 36), 135 (MH$^+$—H$_2$O, 51); HRMS calculated for C$_{10}$H$_{17}$O (MH$^+$): 153.127940, 153.128589 found.

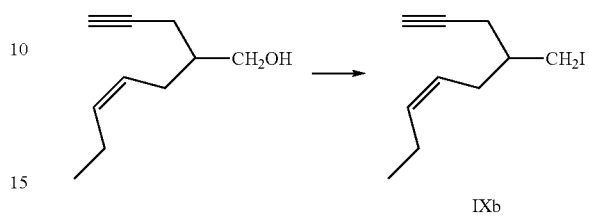

IXb

Triphenylphosphine (725 mg, 2.76 mmol), imidazole (470 mg, 6.9 mmol) and iodine (648 mg, 2.55 mmol) were successively added to a solution of alcohol (350 g, 2.3 mmol) in THF (15 mL), cooled at 0° C. The resulting mixture was stirred at this temperature for 30 minutes and at room temperature for another 30 minutes, and it was subsequently poured over water and extracted with ether. The pooled organic phase was dried with Na$_2$SO$_4$, filtered and concentrated under reduced pressure, and the resulting residue was purified by means of a silica gel flash chromatography column, giving 514 mg of iodide IXb with an 85% yield, R$_f$=0.8 (10% EtOAc/hexanes), colorless oil. $^1$H-NMR (CDCl$_3$, 250 MHz, δ): 5.49, 5.23 (2H, m, H-6, H-7), 3.34 (2H, m, —CH$_2$—I), 2.35 (2H, m, H-8), 2.27 (2H, dd, J=2.6 Hz, J=6.7 Hz, H-3), 2.17 (2H, m, H-5), 2.00 (1H, t, J=2.6 Hz, H-1), 1.55 (1H, m, H-4), 0.96 (3H, t, J=7.5 Hz, H-9). $^{13}$C-NMR (CDCl$_3$, 63 MHz, δ): 134.7 (CH), 125.0 (CH), 81.4 (C≡), 70.2 (C≡), 39.3 (CH), 31.3 (CH$_2$), 23.5 (CH$_2$), 20.8 (CH$_2$), 14.1 (CH$_3$), 13.0 (CH$_2$). EM-IQ$^+$ (m/e, I): 263 (MH$^+$, 0.1), 136 (MH$^+$—I, 11), 121 (15), 107 (55). HRMS calculated for C$_{10}$H$_{16}$ (MH$^+$–I):136.125201, 136.124674 found.

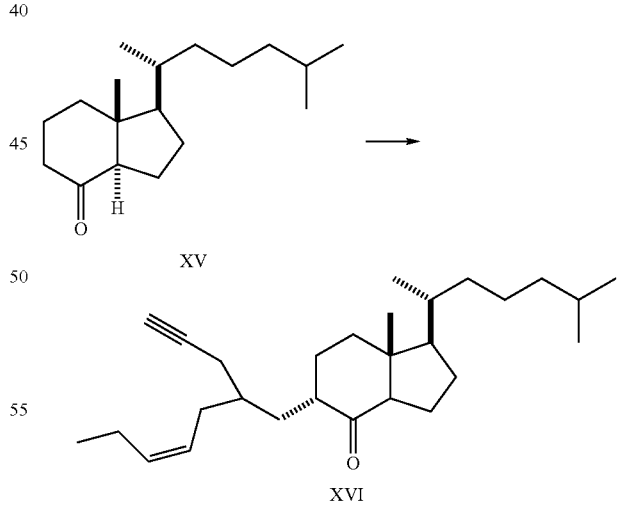

XV

XVI

A solution of ketone XV (0.4 g, 1.45 mmol) in DMF (3 mL) was slowly added to a solution of KHMDS (0.5 M in toluene, 9.0 mL, 4.5 mmol) in DMF (4 mL) cooled at −78° C. The resulting mixture was stirred at this temperature for 30 minutes and a solution of iodide (1.2 g, 4.5 mmol) in DMF (2 mL) was then added. After two hours a saturated NH$_4$Cl solution (4 mL) was added and the aqueous phase was extracted with ether. The pooled ether extracts were washed with a saturated NaCl solution, were dried over $Na_2SO_4$, and concentrated under reduced pressure to give a residue that was purified by means of silica gel flash chromatography (2% EtOAc/hexanes), giving the desired product XVI with a 69% yield. $R_f$=0.6 (10% EtOAc/hexanes), $^1$H-NMR ($CDCl_3$, 250 MHz, δ): 5.43, 5.19 (2H, m, H-4', H-5'), 1.14 (3H, d, J=5.7 Hz, $CH_3$—21), 0.87 (6H, d, J=6.6 Hz, $CH_3$—26 and 27), 0.64 (3H, s, $CH_3$—18). $^{13}$C-NMR ($CDCl_3$, 63 MHz, δ): 214.9 (CO), 133.9 (CH), 126.1 (CH), 82.0 (C≡), 69.7 (C≡), 67.5 ($CH_2$), 57.6 (CH), 53.2 (CH), 50.2 (C), 47.6 (CH), 38.6 (CH), 36.3 ($CH_2$), 35.3 ($CH_2$), 35.1 (CH), 31.05 ($CH_2$), 29.2 ($CH_2$), 27.0 ($CH_2$), 22.7 ($CH_3$), 22.5 ($CH_3$), 21.3 ($CH_2$), 20.6 ($CH_2$), 19.0 ($CH_2$), 17.9 ($CH_3$), 14.2 ($CH_3$), 12.8 ($CH_3$). EM-IQ$^+$ (m/e, I): 399 (MH$^+$, 80), 381 (MH$^+$—$H_2O$, 40). HRMS calculated for $C_{28}H_{47}O$ (MH$^+$): 399.362692, 399.361999 found.

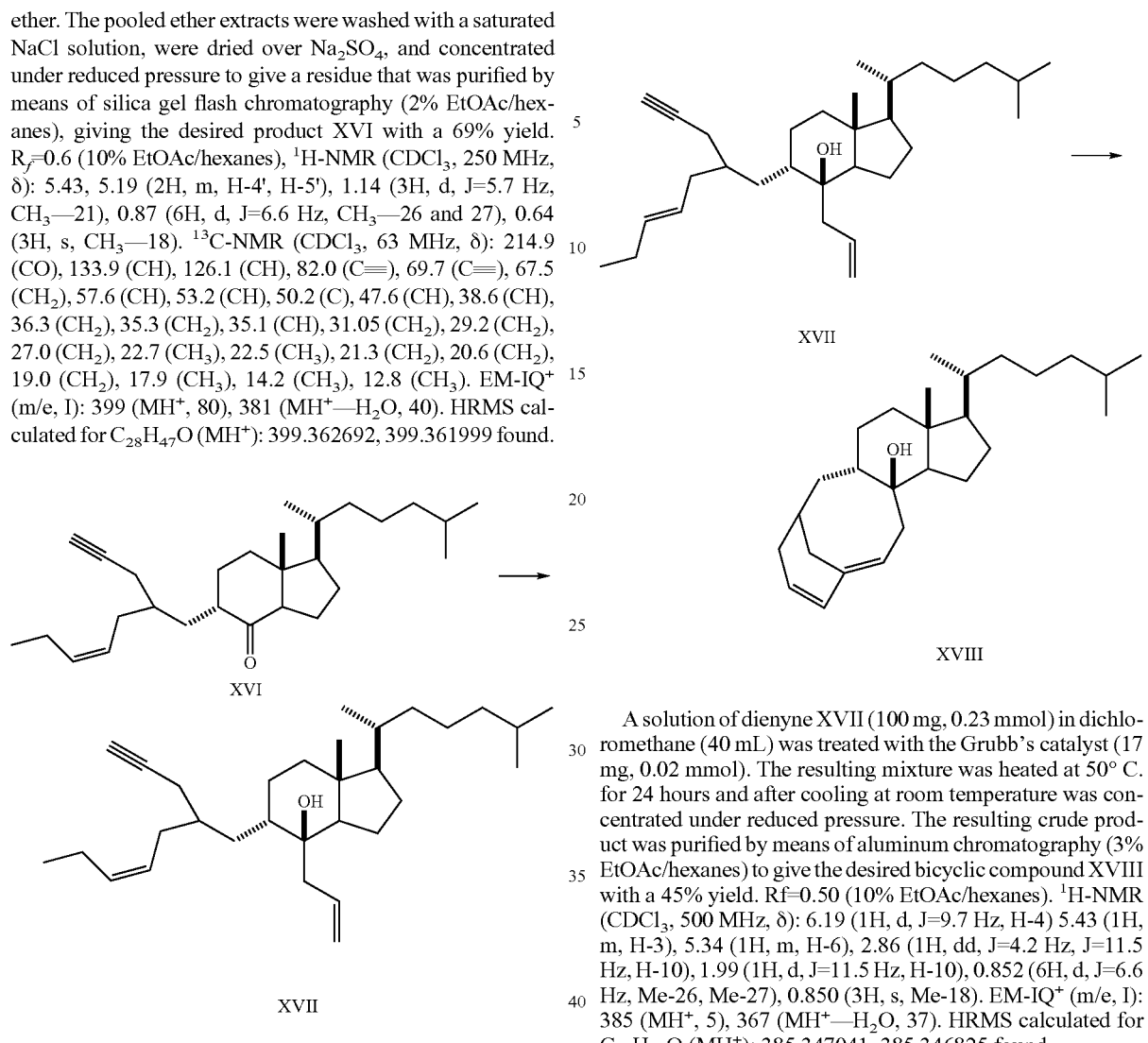

A solution of allylmagnesium bromide (1 M in THF, 2.2 mL, 2.27 mmol) was added to a solution of ketone XVI (200 mg, 0.5 mmol) in THF (5 mL) at −78° C. After two hours a saturated $NH_4Cl$ solution (15 mL) was added and the aqueous phase was extracted with ether. The pooled ether extracts were washed with a saturated NaCl solution, dried over $Na_2SO_4$, and concentrated under reduced pressure to give a residue that was purified by means of silica gel flash chromatography (3% EtOAc/hexanes), giving the desired product XVII with an 80% yield. $R_f$=0.37 (10% EtOAc/hexanes). $R_f$=0.5 (10% EtOAc/hexanes), yellowish oil. $^1$H-NMR ($CDCl_3$, 300 MHz, δ): 5.86 (1H, m, H-6) 5.45, 5.28 (2H, m, H-4', H-5'), 5.16 (2H, m, H-6a), 5.15 (2H, m, H-6a), 0.85 (6H, d, J=6.6. Hz, Me-26, Me-27), 0.88 (3H, s, Me-18). $^{13}$C-NMR ($CDCl_3$, 75 MHz, δ): 133.3 (C), 133.2 (CH), 121.1 (CH), 119.3 ($CH_2$), 83.5 (C≡), 69.2 (C≡), 69.8 ($CH_2$), 67.7 (C), 57.1 (CH), 51.3 (CH), 43.3 (C), 43.4 ($CH_2$), 39.6 (CH), 39.5 ($CH_2$), 35.85 (CH), 35.8 ($CH_2$), 35.2 (CH), 34.6 ($CH_2$), 33.0 ($CH_2$), 31.5 ($CH_2$), 30.25 ($CH_2$), 28.0 (CH), 27.2 ($CH_2$), 23.7 ($CH_2$), 22.8 ($CH_3$), 22.5 ($CH_3$), 20.4 ($CH_2$), 20.0 ($CH_2$), 18.3 ($CH_3$), 17.8 ($CH_3$), 13.4 ($CH_3$). EM-IQ$^+$ (m/e, I): 441 (MH$^+$, 44), 423 (MH$^+$—$H_2O$, 100). HRMS calculated for $C_{32}H_{57}O_2Si$ (MH+): 441.409642, 441.409447 found.

A solution of dienyne XVII (100 mg, 0.23 mmol) in dichloromethane (40 mL) was treated with the Grubb's catalyst (17 mg, 0.02 mmol). The resulting mixture was heated at 50° C. for 24 hours and after cooling at room temperature was concentrated under reduced pressure. The resulting crude product was purified by means of aluminum chromatography (3% EtOAc/hexanes) to give the desired bicyclic compound XVIII with a 45% yield. Rf=0.50 (10% EtOAc/hexanes). $^1$H-NMR ($CDCl_3$, 500 MHz, δ): 6.19 (1H, d, J=9.7 Hz, H-4) 5.43 (1H, m, H-3), 5.34 (1H, m, H-6), 2.86 (1H, dd, J=4.2 Hz, J=11.5 Hz, H-10), 1.99 (1H, d, J=11.5 Hz, H-10), 0.852 (6H, d, J=6.6 Hz, Me-26, Me-27), 0.850 (3H, s, Me-18). EM-IQ$^+$ (m/e, I): 385 (MH$^+$, 5), 367 (MH$^+$—$H_2O$, 37). HRMS calculated for $C_{27}H_{45}O$ (MH$^+$): 385.347041, 385.346825 found.

The invention claimed is:
1. A compound of formula (1),

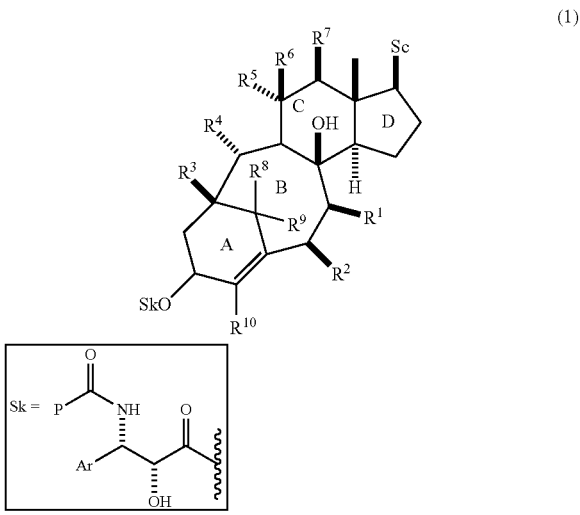

wherein:
R$^1$, R$^2$, R$^3$, R$^4$, R$^5$, R$^6$, R$^7$, R$^8$, R$^9$ and R$^{10}$ can independently be a hydrogen atom, an acyloxy, alkyloxy, aryloxy, alkylthio, arylthio or alkyl group with C$_1$-C$_{10}$ chains;

Sc is a characteristic side chain of steroids, a linear or branched alkyl radical with 1-12 carbon atoms, an alkenyl radical with 2 to 12 carbon atoms, an alkynyl radical with 3 to 12 carbon atoms, a cycloalkyl radical with 3 to 6 carbon atoms, a cycloalkenyl radical with 4 to 6 carbon atoms, or a bicycloalkyl radical with 7 to 10 carbon atoms; and Sk is an amino acid chain analogous to that of to taxanes, in which P is a phenyl group or an alkoxy radical with alkyl chains with 1 to 10 carbon atoms, alkenyl chains with 3 to 10 carbon atoms alkynyl chains with 3 to 10 carbon atoms, cycloalkyl chains with 4 to 7 carbon atoms in the ring cycloalkenyl chains with 4 to 7 carbon atoms in the ring, a phenyl or a heterocyclic compound, and Ar is an aromatic moiety.

2. A compound of formula (2),

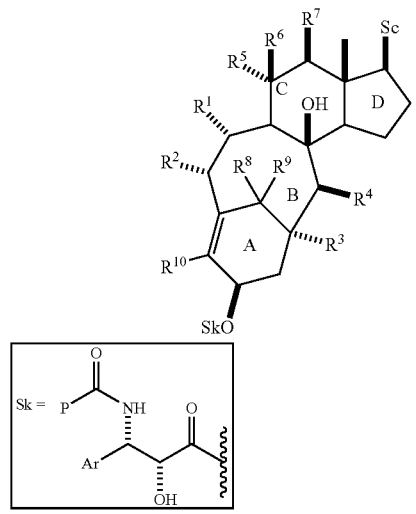

(2)

wherein:
R$^1$, R$^2$, R$^3$, R$^4$, R$^5$, R$^6$, R$^7$, R$^8$, R$^9$ and R$^{10}$ can independently be a hydrogen atom, an acyloxy, alkyloxy, aryloxy, alkylthio, arylthio, or alkyl group with C1-C10 chains;

Sc is a characteristic side chain of steroids, a linear or branched alkyl radical with 1-12 carbon atoms, an alkenyl radical with 2 to 12 carbon atoms, an alkynyl radical with 3 to 12 carbon atoms, a cycloalkyl radical with 3 to 6 carbon atoms, a cycloalkenyl radical with 4 to 6 carbon atoms, or a bicycloalkyl radical with 7 to 10 carbon atoms;

Sk is an amino acid chain analogous to that of to taxanes, in which P is a phenyl group or an alkoxy radical with alkyl chains with 1 to 10 carbon atoms, alkenyl chains with 3 to 10 carbon atoms alkynyl chains with 3 to 10 carbon atoms, cycloalkyl chains with 4 to 7 carbon atoms in the ring cycloalkenyl chains with 4 to 7 carbon atoms in the ring, a phenyl or a heterocyclic compound, and Ar is an aromatic moiety.

3. A process of manufacturing a compound of formula (1)

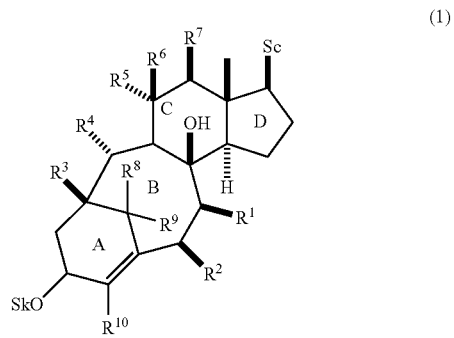

(1)

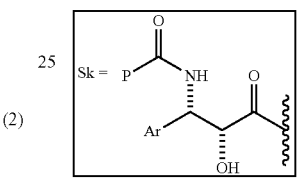

comprising:
a) alkylation of the kinetic enolate of the ketones carrying the CD ring of steroids, of formula (3) to produce a compound of formula (5),

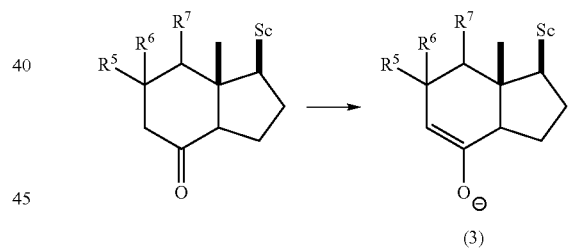

(3)

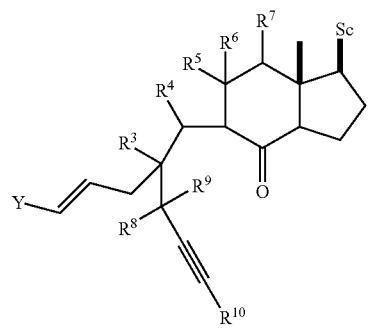

(5)

b) alkylation of the compound of formula (5) to produce a dienyne of formula (6)

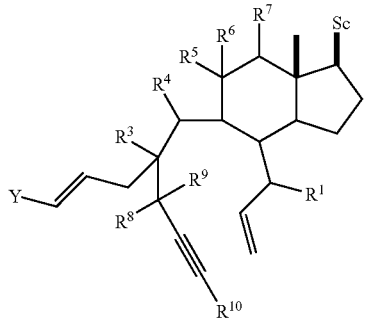
(6)

c) metathesis cyclization reaction of the dienyne of formula (6) catalyzed by metal carbene catalysts.

4. A process of manufacturing a compound of formula (2)

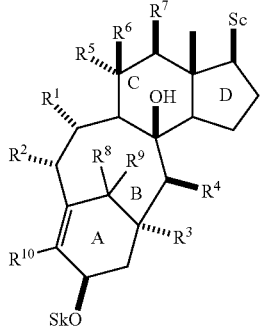
(2)

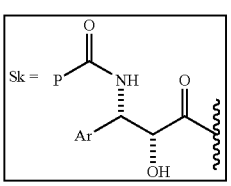

comprising:

a) alkylation of a kinetic enolate of a ketone of formula (3) to produce a compound of formula (9),

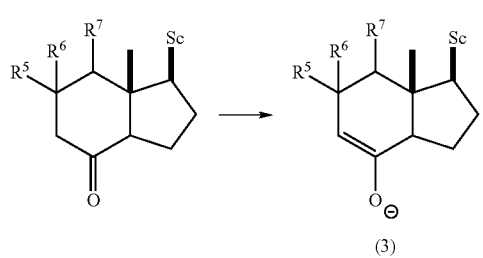
(3)

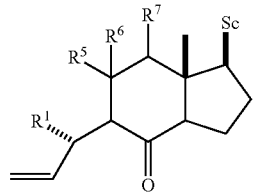
(9)

b) alkylation of the carbonyl group of the compound of formula (9) to produce a dienyne of formula (11),

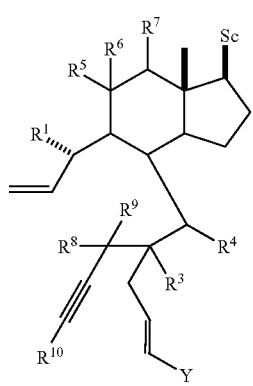
(11)

c) metathesis cyclization reaction of the dienyne of formula (11) catalyzed by metal carbene catalyst.

5. The compound according claim 1, wherein at least one of $R^1$, $R^2$, $R^3$, $R^4$, $R^5$, $R^6$, $R^7$, $R^8$, $R^9$ or $R^{10}$ is an acyloxy, alkyloxy, aryloxy, alkylthio, arylthio or alkyl group with $C_1$-$C_{10}$ chains substituted by a linear or branched alkyl with 1-10 carbon atoms,
an alkenyl with 2 to 10 carbon atoms,
an alkynyl with 3 to 10 carbon atoms,
a cycloalkyl with 3 to 6 carbon atoms,
a cycloalkenyl with 4 to 6 carbon atoms, or
a bicycloalkyl with 7 to 10 carbon atoms.

6. The compound according to claim 5, wherein said linear or branched alkyl with 1-10 carbon atoms, alkenyl with 2 to 10 carbon atoms, alkynyl with 3 to 10 carbon atoms, cycloalkyl with 3 to 6 carbon atoms, cycloalkenyl with 4 to 6 carbon atoms, or bicycloalkyl with 7 to 10 carbon atoms is substituted by one or several substituents selected from the group of:

a halogen,
an hydroxy group,
an alkoxy radical containing 1 to 4 carbon atoms,
a piperidinyl,
a morpholinyl,
a piperazinyl-1,
a cycloalkyl with 3 to 6 carbon atoms,
a cycloalkenyl with 4 to 6 carbon atoms,
a phenyl,
a cyano,
a nitro,
a carboxy,
an alkoxycarbonyl, the alkyl part of which contains 1 to 4 carbon atoms, and
a phenyl.

7. The compound according to claim 6, wherein said piperazinyl-1 is substituted at -4 by an alkyl radical with 1 to 4 carbon atoms or by a phenylalkyl radical, the alkyl part of which contains 1 to 4 carbon atoms.

8. A compound according to claim 6, wherein said phenyl is substituted by one or several radicals, chosen from
an alkyl radical with 1 to 4 carbon atoms,
an alkoxy radical containing 1 to 4 carbon atoms, and
a saturated or unsaturated nitrogenous heterocyclic radical containing 5 or 6 members.

9. The compound according to claim 8, wherein said saturated or unsaturated nitrogenous heterocyclic radical containing 5 or 6 members is substituted by one or several alkyl radicals with 1 to 4 carbon atoms.

10. The compound according to claim 5, wherein at least one of said cycloalkyl, cycloalkenyl or bicycloalkyl radicals is substituted by one or several alkyl radicals with 1 to 4 carbon atoms.

11. The compound according to claim 1, wherein Sc is a linear or branched alkyl radical with 1-12 carbon atoms, an alkenyl with 2 to 12 carbon atoms, an alkynyl with 3 to 12 carbon atoms, a cycloalkyl with 3 to 6 carbon atoms, a cycloalkenyl with 4 to 6 carbon atoms or a bicycloalkyl with 7 to 10 carbon atoms substituted by one or several identical or different substituents chosen from
a halogen,
an hydroxy group,
an alkoxy radical containing 1 to 4 carbon atoms,
a piperidinyl,
a morpholinyl,
a piperazinyl-1,
a cycloalkyl with 3 to 6 carbon atoms,
a cycloalkenyl with 4 to 6 carbon atoms,
a phenyl,
a cyano,
a nitro,
a carboxy,
an alkoxycarbonyl, the alkyl part of which contains 1 to 4 carbon atoms, and
a phenyl.

12. The compound according to claim 11, wherein said piperazinyl-1 is substituted at -4 by an alkyl radical with 1 to 4 carbon atoms or by a phenylalkyl radical, the alkyl part of which contains 1 to 4 carbon atoms.

13. The compound according to claim 11, wherein said phenyl is substituted by one or several radicals, chosen from
an alkyl radical with 1 to 4 carbon atoms,
an alkoxy radical containing 1 to 4 carbon atoms, and
a saturated or unsaturated nitrogenous heterocyclic radical with 5 or 6 members.

14. The compound according to claim 13, wherein said saturated or unsaturated nitrogenous heterocyclic radical with 5 or 6 members is substituted by one or several alkyl radicals with 1 to 4 carbon atoms.

15. The compound according to claim 1, wherein Sc is a cycloalkyl with 3 to 6 carbon atoms, a cycloalkenyl with 4 to 6 carbon atoms or a bicycloalkyl with 7 to 10 carbon atoms substituted by one or several alkyl radicals containing 1 to 4 carbon atoms.

16. The compound according claim 2, wherein at least one of $R^1$, $R^2$, $R^3$, $R^4$, $R^5$, $R^6$, $R^7$, $R^8$, $R^9$ or $R^{10}$ is an acyloxy, alkyloxy, aryloxy, alkylthio, arylthio or alkyl group with $C_1$-$C_{10}$ chains substituted by
a linear or branched alkyl with 1-10 carbon atoms,
an alkenyl with 2 to 10 carbon atoms,
an alkynyl with 3 to 10 carbon atoms,
a cycloalkyl with 3 to 6 carbon atoms,
a cycloalkenyl with 4 to 6 carbon atoms, or
a bicycloalkyl with 7 to 10 carbon atoms.

17. The compound according to claim 16, wherein said linear or branched alkyl with 1-10 carbon atoms, alkenyl with 2 to 10 carbon atoms, alkynyl with 3 to 10 carbon atoms, cycloalkyl with 3 to 6 carbon atoms, cycloalkenyl with 4 to 6 carbon atoms, or bicycloalkyl with 7 to 10 carbon atoms is substituted by one or several identical or different substituents selected from the group of:
a halogen,
an hydroxy group,
an alkoxy radical containing 1 to 4 carbon atoms,
a piperidinyl,
a morpholinyl,
a piperazinyl-1,
a cycloalkyl with 3 to 6 carbon atoms,
a cycloalkenyl with 4 to 6 carbon atoms,
a phenyl,
a cyano,
a nitro,
a carboxy,
an alkoxycarbonyl, the alkyl part of which contains 1 to 4 carbon atoms, and
a phenyl.

18. The compound according to claim 17, wherein said piperazinyl-1 is substituted at -4 by an alkyl radical with 1 to 4 carbon atoms or by a phenylalkyl radical, the alkyl part which contains 1 to 4 carbon atoms.

19. The compound according to claim 17, wherein said phenyl is substituted by one or several identical or different radicals, chosen from
an alkyl radical with 1 to 4 carbon atoms,
an alkoxy radical containing 1 to 4 carbon atoms, and
a saturated or unsaturated nitrogenous heterocyclic radical containing 5 or 6 members.

20. The compound according to claim 19, wherein said saturated or unsaturated nitrogenous heterocyclic radical containing 5 or 6 members is substituted by one or several alkyl radicals with 1 to 4 carbon atoms.

21. The compound according to claim 16, wherein at least one of said cycloalkyl, cycloalkenyl or bicycloalkyl radicals is substituted by one or several alkyl radicals with 1 to 4 carbon atoms.

22. The compound according to claim 2, wherein Sc is a linear or branched alkyl radical with 1-12 carbon atoms, an alkenyl with 2 to 12 carbon atoms, an alkynyl with 3 to 12 carbon atoms, a cycloalkyl with 3 to 6 carbon atoms, a cycloalkenyl with 4 to 6 carbon atoms or a bicycloalkyl with 7 to 10 carbon atoms substituted by one or several substituents chosen from
a halogen,
an hydroxy group,
an alkoxy radical containing 1 to 4 carbon atoms,
a piperidinyl,
a morpholinyl,
a piperazinyl-1,
a cycloalkyl with 3 to 6 carbon atoms,
a cycloalkenyl with 4 to 6 carbon atoms,
a phenyl,
a cyano,
a nitro,
a carboxy,
an alkoxycarbonyl, the alkyl part of which contains 1 to 4 carbon atoms, and
a phenyl.

23. The compound according to claim 22, wherein said piperazinyl-1 is substituted at -4 by an alkyl radical with 1 to 4 carbon atoms or by a phenylalkyl radical, the alkyl part of which contains 1 to 4 carbon atoms.

24. The compound according to claim 22, wherein said phenyl is substituted by one or several radicals, chosen from
- an alkyl radical with 1 to 4 carbon atoms,
- an alkoxy radical containing 1 to 4 carbon atoms, and
- a saturated or unsaturated nitrogenous heterocyclic radical with 5 or 6 members.

25. The compound according to claim 24, wherein said saturated or unsaturated nitrogenous heterocyclic radical with 5 or 6 members is substituted by one or several alkyl radicals with 1 to 4 carbon atoms.

26. The compound according to claim 2, wherein Sc is a cycloalkyl with 3 to 6 carbon atoms, a cycloalkenyl with 4 to 6 carbon atoms or a bicycloalkyl with 7 to 10 carbon atoms substituted by one or several alkyl radicals containing 1 to 4 carbon atoms.

27. The process according to claim 3, wherein said metal carbene catalyst of step c) is Grubbs's catalyst.

28. A process according to claim 3, comprising an additional final step of modification of functional groups, said modification being selected among an oxidation, reduction, esterification, alkylation or isomerization reactions.

29. The process according to claim 4, wherein said metal carbene catalyst of step c) is Grubbs's catalyst.

30. The process according to claim 4, comprising an additional final step of modification of functional groups, said modification being selected among an oxidation, reduction, esterification, alkylation or isomerization reactions.

31. The method of treating cancer which comprises administering an effective amount of a compound according to claim 1 in a medicine to a patient in need thereof 32. The method of treating cancer which comprises administering an effective amount of a compound according to claim 2 in a medicine to a patient in need thereof.

* * * * *